United States Patent
DeBonte et al.

(10) Patent No.: US 7,262,343 B1
(45) Date of Patent: Aug. 28, 2007

(54) PLANTS HAVING MUTANT DELTA-12 DESATURASE SEQUENCES THAT CONFER ALTERED FATTY ACID PROFILES

(75) Inventors: Lorin R DeBonte, Fort Collins, CO (US); Guo-Hua Miao, Johnston, IA (US); Zhegong Fan, Colorado Springs, CO (US)

(73) Assignee: Cargill, Incorporated, Wayzata, MN (US)

( * ) Notice: Subject to any disclaimer, the term of this patent is extended or adjusted under 35 U.S.C. 154(b) by 0 days.

(21) Appl. No.: 09/064,277

(22) Filed: Apr. 22, 1998

Related U.S. Application Data

(60) Division of application No. 08/572,027, filed on Dec. 14, 1995, now Pat. No. 7,135,614, which is a continuation-in-part of application No. 08/416,497, filed on Apr. 4, 1995, now Pat. No. 5,668,299, which is a continuation of application No. 08/170,886, filed on Dec. 21, 1993, now abandoned, which is a continuation-in-part of application No. 07/739,965, filed on Aug. 5, 1991, now abandoned, which is a continuation-in-part of application No. 07/575,542, filed on Aug. 30, 1990, now abandoned.

(51) Int. Cl.
*A01H 5/00* (2006.01)
(52) U.S. Cl. .................................... 800/306
(58) Field of Classification Search ............... 800/289, 800/306, 281
See application file for complete search history.

(56) References Cited

U.S. PATENT DOCUMENTS

| 4,627,192 | A |  | 12/1986 | Fick |  |
|---|---|---|---|---|---|
| 4,948,811 | A |  | 8/1990 | Spinner et al. |  |
| 5,387,758 | A |  | 2/1995 | Wong et al. |  |
| 5,434,283 | A |  | 7/1995 | Wong et al. |  |
| 5,668,299 | A | * | 9/1997 | Debonte et al. | 800/264 |
| 6,342,658 | B1 | * | 1/2002 | DeBonte et al. | 800/306 |
| 6,372,965 | B1 |  | 4/2002 | Lightner et al. |  |

FOREIGN PATENT DOCUMENTS

| EP | 323 753 | 7/1989 |
|---|---|---|
| WO | WO91/15578 | 10/1991 |
| WO | WO93/11245 | 6/1993 |
| WO | WO94/11516 | 5/1994 |

OTHER PUBLICATIONS www.brassica.info/genomesize.htm.*
Taxonomy Browser, 2005, http://www.ncbi.nlm.nih.gov/Taxonomy/Browser/wwwtax.cgi.*
Conner et al., Coronary Heart Disease: Prevention, Complications, and Treatment, 43-46, 1985.
F.H. Mattson, *J. Am. Diet. Assoc.*, 89, 387-390, 1989.
Mensink et al., *New England J. Med.*, 321, 436-441, 1989.
S.M. Grundy, *New England J. Med.*, 314, 745-748, 1986.
Garg et al., *New England J. Med.*, 319, 829-834, 1988.
Williams et al., *J. Am. Med. Assoc.*, 257, 3251-3256, 1987.
*Circulation*, vol. XLI, Suppl. I, Keys, A., ed., pp. I162-I183 (1970).
Pleines and Friedt, *Fat Sci. Technol.*, 90(5), 167-171, 1988.
Rakow and McGregor, *J. Amer. Oil Chem. Soc.*, 50, 400-403, Oct. 1973.
Roy and Tarr, *Pflansenzuchtg*, 95(3), 201-209, 1985.
Roy and Tarr, *Plant Breeding*, 98, 89-96, 1987.
Canvin, *Can. J. Botany*, 43, 63-69, 1965.
G.Z. Gaul, *Radiation Botany*, 4, 155-232, 1964.
G.Z. Rakow, *Pflanzenzuchtg*, 69, 62-82, 1973.
Scarth et al., *Can. J. Plant Sci.*, 68, 509-511, 1988.
Downey et al., *Can. J. Plant Sci.*, 43, 271, 1963.
B.R. Stefanson, In; High and Low Erucic Acid Rapeseed Oils, Ed. N.T. Kenthies, Academic Press Inc., Canada, 145-159, 1983.
G. Robbelen, In; Biotechnology for the Oils and Fats Industry, *American Oil Chemists Society*, 97-105, 1984.
Tremolieres et al., *Phytochemistry*, 21(1), 41-45, 1982.
Robbelen et al., *Pflanzenauchtg*, 75, 93-105, 1985.
Robbelen et al., Proceedings of the International Conference on the Scientific, Technology, and Marketing of Rapeseed and Rapeseed Products, Sep. 20-23, 1970.
Pleines et al., Abstract of 43rd Lecture Meeting of Deutsche Gesellschaft fur Feltwissenschaft in Hamburg, Sep. 30-Oct. 11, 1987.
Brunklaus-Jung et al., *Plant Breeding*, 98, 9-16, 1987.
Hoffman et al., *Theor. Appl. Genet.*, 61, 225-232, 1982.
Kondra et al., Selection for Oleic, Linoleic and Linolenic Acid Content in $F_2$ Populations of Rape, *Can. J. Plant Sci.*, 56, 961-966, 1976.
Svalöf 1886-1986 Research and Results in Plant Breeding, pp. 173-184 LTs forlag, Stockholm.
Okuley et al., *Plant Cell*, 6:147-158, 1994.
Arondel et al., *Science*, 258:1153-1155, 1992.
Yadav et al., *Plant Physiol.*, 103:467-476, 1993.
Hitz et al., *Plant Physiol.*, 103:635-641, 1994.
Töpfer et al., *Science*, 268:681-686, 1995.
Shanklin et al., *Biochemistry*, 33:12787, 1994.
Kirk-Othmer Encyclopedia of Chemical Technol., 3rd Edition, 9, 795-831, 1980.
Pleines et al., Abstract of Proceedings of the 7th International Rapeseed Congress, Pozman, Poland, May 11-14, 1987.

* cited by examiner

*Primary Examiner*—Anne Kubelik
(74) *Attorney, Agent, or Firm*—Fish & Richardson P.C.

(57) ABSTRACT

Brassicaceae plants are disclosed that contain a mutation in a delta-12 fatty acid desaturase gene and that have altered fatty acid composition in seeds. In one embodiment, a Brassicaceae plant contains a mutation in a region having the conserved motif His-Xaa-Xaa-Xaa-His, found in delta-12 and delta-15 fatty acid desaturases. A preferred motif has the sequence His-Glu-Cys-Gly-His. A preferred mutation in this motif has the amino acid sequence His-Lys-Cys-Gly-His.

16 Claims, 1 Drawing Sheet

PLANTS HAVING MUTANT DELTA-12 DESATURASE SEQUENCES THAT CONFER ALTERED FATTY ACID PROFILES

CROSS REFERENCE TO RELATED APPLICATIONS

This is a divisional of U.S. application Ser. No. 08/572,027, filed Dec. 14, 1995 now U.S. Pat. No. 7,135,614, which is a continuation-in-part of U.S. Ser. No. 08/416,497, filed Apr. 4, 1995 now U.S. Pat. No. 5,668,299, which is a continuation of U.S. Ser. No. 08/170,886, filed Dec. 21, 1993, now abandoned, which is a continuation-in-part of U.S. Ser. No. 07/739,965, filed Aug. 5, 1991, now abandoned, which is a continuation-in-part of U.S. Ser. No. 07/575,542, filed Aug. 30, 1990, now abandoned.

TECHNICAL FIELD

This invention relates to *Brassica* seeds and plants having mutant sequences which confer altered fatty acid profiles on the seed oil. More particularly, the invention relates to mutant delta-12 and delta-15 fatty acid desaturase sequences in such plants which confer such profiles.

BACKGROUND OF THE INVENTION

Diets high in saturated fats increase low density lipoproteins (LDL) which mediate the deposition of cholesterol on blood vessels. High plasma levels of serum cholesterol are closely correlated with atherosclerosis and coronary heart disease (Conner et al., Coronary Heart Disease: Prevention, Complications, and Treatment, pp. 43-64, 1985). By producing oilseed *Brassica* varieties with reduced levels of individual and total saturated fats in the seed oil, oil-based food products which contain less saturated fats can be produced. Such products will benefit public health by reducing the incidence of atherosclerosis and coronary heart disease.

The dietary effects of monounsaturated fats have also been shown to have dramatic effects on health. Oleic acid, the only monounsaturated fat in most edible vegetable oils, lowers LDL as effectively as linoleic acid, but does not affect high density lipoproteins (HDL) levels (Mattson, F. H., J. Am. Diet. Assoc., 89:387-391, 1989; Mensink et al., New England J. Med., 321:436-441, 1989). Oleic acid is at least as effective in lowering plasma cholesterol as a diet low in fat and high in carbohydrates (Grundy, S. M., New England J. Med., 314:745-748, 1986; Mensink et al., New England J. Med., 321:436-441, 1989). In fact, a high oleic acid diet is preferable to low fat, high carbohydrate diets for diabetics (Garg et al., New England J. Med., 319:829-834, 1988). Diets high in monounsaturated fats are also correlated with reduced systolic blood pressure (Williams et al., J. Am. Med. Assoc., 257:3251-3256, 1987). Epidemiological studies have demonstrated that the "Mediterranean" diet, which is high in fat and monounsaturates, is not associated with coronary heart disease (Keys, A., Circulation, 44(Suppl):1, 1970).

Many breeding studies have been conducted to improve the fatty acid profile of *Brassica* varieties. Pleines and Freidt, Fat Sci. Technol., 90(5), 167-171 (1988) describe plant lines with reduced $C_{18:3}$ levels (2.5-5.8%) combined with high oleic content (73-79%). Rakow and McGregor, J. Amer. Oil Chem. Soc., 50, 400-403 (October 1973) discuss problems associated with selecting mutants for linoleic and linolenic acids. In. Can. J. Plant Sci., 68, 509-511 (April 1988) Stellar summer rape producing seed oil with 3% linolenic acid and 28% linoleic acid is disclosed. Roy and Tarr, Z. Pflanzenzuchtg, 95(3), 201-209 (1985) teaches transfer of genes through an interspecific cross from *Brassica juncea* into *Brassica napus* resulting in a reconstituted line combining high linoleic with low linolenic acid content. Roy and Tarr, Plant Breeding, 98, 89-96 (1987) discuss prospects for development of *B. napus* L. having improved linoleic and linolenic acid content. European Patent application 323,751 published Jul. 12, 1989 discloses seeds and oils having greater than 79% oleic acid combined with less than 3.5% linolenic acid. Canvin, Can. J. Botany, 43, 63-69 (1965) discusses the effect of temperature on the fatty acid composition of oils from several seed crops including rapeseed.

Mutations typically are induced with extremely high doses of radiation and/or chemical mutagens (Gaul, H. Radiation Botany (1964) 4:155-232). High dose levels which exceed LD50, and typically reach LD90, led to maximum achievable mutation rates. In mutation breeding of *Brassica* varieties high levels of chemical mutagens alone or combined with radiation have induced a limited number of fatty acid mutations (Rakow, G. Z. Pflanzenzuchtg (1973) 69:62-82). The low α-linolenic acid mutation derived from the Rakow mutation breeding program did not have direct commercial application because of low seed yield. The first commercial cultivar using the low α-linolenic acid mutation derived in 1973 was released in 1988 as the variety Stellar (Scarth, R. et al., Can. J. Plant Sci. (1988) 68:509-511). Stellar was 20% lower yielding than commercial cultivars at the time of its release.

Canola-quality oilseed *Brassica* varieties with reduced levels of saturated fatty acids in the seed oil could be used to produce food products which promote cardiovascular health. Canola lines which are individually low in palmitic and stearic acid content or low in combination will reduce the levels of saturated fatty acids. Similarly, *Brassica* varieties with increased monounsaturate levels in the seed oil, and products derived from such oil, would improve lipid nutrition. Canola lines which are low in linoleic acid tend to have high oleic acid content, and can be used in the development of varieties having even higher oleic acid content.

Increased palmitic acid content provides a functional improvement in food applications. Oils high in palmitic acid content are particularly useful in the formulation of margarines. Thus, there is a need for manufacturing purposes for oils high in palmitic acid content.

Decreased α-linolenic acid content provides a functional improvement in food applications. Oils which are low in linolenic acid have increased stability. The rate of oxidation of lipid fatty acids increases with higher levels of linolenic acid leading to off-flavors and off-odors in foods. There is a need in the food industry for oils low in alpha linolenic acid.

Delta-12 fatty acid desaturase (also known as oleic desaturase) is involved in the enzymatic conversion of oleic acid to linoleic acid. Delta-15 fatty acid desaturase (also known as linoleic acid desaturase) is involved in the enzymatic conversion of linoleic acid to α-linolenic acid. A microsomal delta-12 desaturase has been cloned and characterized using T-DNA tagging. Okuley, et al., Plant Cell 6:147-158 (1994). The nucleotide sequences of higher plant genes encoding microsomal delta-12 fatty acid desaturase are described in Lightner et al., WO94/11516. Sequences of higher plant genes encoding microsomal and plastid delta-15 fatty acid desaturases are disclosed in Yadav, N., et al., Plant Physiol., 103:467-476 (1993), WO 93/11245 and Arondel, V. et al., Science, 258:1353-1355 (1992). However, there are no teachings that disclose mutations in delta-12 or delta-15 fatty acid desaturase coding sequences from plants. Furthermore, no methods have been described for developing plant lines that contain delta-12 or delta-15 fatty acid desaturase gene sequence mutations effective for altering the fatty acid composition of seeds.

SUMMARY OF THE INVENTION

The present invention comprises canola seeds, plant lines producing seeds, and plants producing seed, said seeds having a maximum content of FDA saturates of about 5% and a maximum erucic acid content of about 2% based upon total extractable oil and belonging to a line in which said saturates content has been stabilized for both the generation to which the seed belongs and its parent generation. Progeny of said seeds and canola oil having a maximum erucic acid content of about 2%, based upon total extractable oil, are additional aspects of this invention. Preferred are seeds, plant lines producing seeds, and plants producing seeds, said seeds having an FDA saturates content of from about 4.2% to about 5.0% based upon total extractable oil.

The present invention further comprises *Brassica* seeds, plant lines producing seeds, and plants producing seeds, said seeds having a minimum oleic acid content of about 71% based upon total extractable oil and belonging to a line in which said oleic acid content has been stabilized for both the generation to which the seed belongs and its parent generation. A further aspect of this invention is such high oleic acid seeds additionally having a maximum erucic acid content of about 2% based upon total extractable oil. Progeny of said seeds; and *Brassica* oil having 1) a minimum oleic acid content of about 71% or 2) a minimum oleic acid content of about 71% and a maximum erucic content of about 2% are also included in this invention. Preferred are seeds, plant lines producing seeds, and plants producing seeds, said seeds having an oleic acid content of from about 71.2% to about 78.3% based upon total extractable oil.

The present invention further comprises canola seeds, plant lines producing seeds, and plants producing seeds, said seeds having a maximum linoleic acid content of about 14% and a maximum erucic acid content of about 2% based upon total extractable oil and belonging to a line in which said acid content is stabilized for both the generation to which the seed belongs and its parent generation. Progeny of said seeds and canola oil having a maximum linoleic acid content of about 14% and a maximum erucic acid content of about 2%, are additional aspects of this invention. Preferred are seeds, plant lines producing seeds, and plants producing seeds, said seeds having a linoleic acid content of from about 8.4% to about 9.4% based upon total extractable oil.

The present invention further comprises *Brassica* seeds, plant lines producing seeds, and plants producing seeds, said seeds having a maximum palmitic acid content of about 3.5% and a maximum erucic acid content of about 2% based on total extractable oil and belonging to a line in which said acid content is stabilized for both the generation to which the seed belongs and its parent generation. Progeny of said seeds and canola having a maximum palmitic acid content of about 3.5% and a maximum erucic acid content of about 2%, are additional aspects of this invention. Preferred are seeds, plant lines producing seeds, and plants producing seeds, said seeds having a palmitic acid content of from about 2.7% to about 3.1% based upon total extractable oil.

The present invention further comprises *Brassica* seeds, plant lines producing seeds, and plants producing seeds, said seeds having a minimum palmitic acid content of about 9.0% based upon total extractable oil and belonging to a line in which said acid content is stabilized for both the generation to which the seed belongs and its parent generation. A further aspect of this invention is such high palmitic acid seeds additionally having a maximum erucic acid content of about 2% based upon total extractable oil. Progeny of said seeds; and *Brassica* oil having 1) a minimum palmitic acid content of about 9.0%, or 2) a minimum palmitic acid content of about 9.0% and a maximum erucic acid content of about 2% are also included in this invention. Preferred are seeds, plant lines producing seeds, and plants producing seeds, said seeds having a palmitic acid content of from about 9.1% to about 11.7% based upon total extractable oil.

The present invention further comprises *Brassica* seeds, plant lines producing seeds, and plants producing seeds, said seeds having a maximum stearic acid content of about 1.1% based upon total extractable oil and belonging to a line in which said acid content is stabilized for both the generation to which the seed belongs and its parent generation. Progeny of said seeds have a canola oil having a maximum stearic acid content of about 1.1% and maximum erucic acid content of about 2%. Preferred are seeds, plant lines producing seeds, and plants producing seeds having a palmitic acid content of from about 0.8% to about 1.1% based on total extractable oil.

The present invention further comprises *Brassica* seeds, plant lines producing seeds, and plants producing seeds, said seeds having a sum of linoleic acid content and linolenic acid content of a maximum of about 14% based upon total extractable oil and belonging to a line in which said acid content is stabilized for both the generation to which the seed belongs and its parent generation. Progeny of said seeds have a canola oil having a sum of linoleic acid content and linolenic acid content of a maximum of about 14% and a maximum erucic acid content of about 2%. Preferred are seeds, plant lines producing seeds, and plants producing seeds having a sum of linoleic acid content and linolenic acid content of from about 11.8% to about 12.5% based on total extractable oil.

The invention further comprises Brassicaceae or *Helianthus* seeds, plants and plant lines having at least one mutation that controls the levels of unsaturated fatty acids in plants. One embodiment of the invention is an isolated nucleic acid fragment comprising a nucleotide sequence encoding a mutant delta-12 fatty acid desaturase conferring increased levels of oleic acid when the fragment is present in a plant. A preferred sequence comprises a mutant sequence as shown in SEQ ID NO:3. Another embodiment of the invention is an isolated nucleic acid fragment comprising a nucleotide sequence encoding a mutant delta-15 fatty acid desaturase. A plant in this embodiment may be soybean, oilseed *Brassica* species, sunflower, castor bean or corn. The mutant sequence may be derived from, for example, a *Brassica napus, Brassica rapa, Brassica juncea* or *Helianthus* delta-12 or delta-15 gene.

Another embodiment of the invention involves a method of producing a Brassicaceae or *Helianthus* plant line comprising the steps of: (a) inducing mutagenesis in cells of a starting variety of a Brassicaceae or *Helianthus* species; (b) obtaining progeny plants from the mutagenized cells; (c) identifying progeny plants that contain a mutation in a delta-12 or delta-15 fatty acid desaturase gene; and (d) producing a plant line by selfing.

Yet another embodiment of the invention involves a method of producing plant lines containing altered levels of unsaturated fatty acids comprising: (a) crossing a first plant with a second plant having a mutant delta-12 or delta-15 fatty acid desaturase; (b) obtaining seeds from the cross of step (a); (c) growing fertile plants from such seeds; (d) obtaining progeny seed the plants of step (c); and (e) identifying those seeds among the progeny that have altered fatty acid composition. Suitable plants are soybean, rapeseed, sunflower, safflower, castor bean and corn. Preferred plants are rapeseed and sunflower.

The invention is also embodied in vegetable oil obtained from plants disclosed herein, which vegetable oil has an altered fatty acid composition.

DESCRIPTION OF THE PREFERRED EMBODIMENTS

Figure 1:
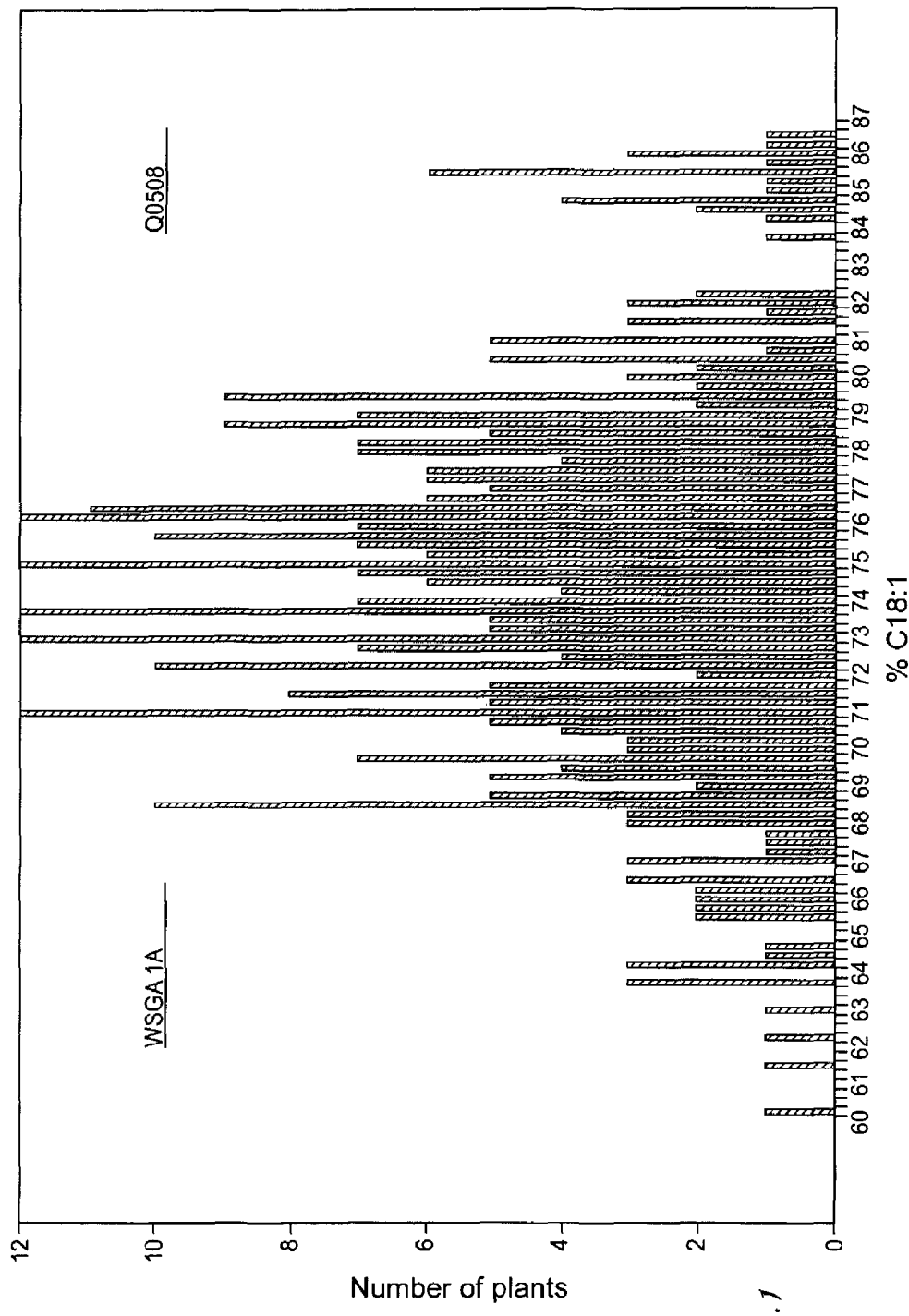
FIG. 1 is a histogram showing the frequency distribution of seed oil oleic acid ($C_{18:1}$) content in a segregating population of a Q508 X Westar cross. The bar labeled WSGA 1A represents the $C_{18:1}$ content of the Westar parent. The bar labeled Q508 represents the $C_{18:1}$ content of the Q508 parent.

The U.S. Food and Drug Administration defines saturated fatty acids as the sum of lauric ($C_{12:0}$), myristic ($C_{14:0}$), palmitic ($C_{16:0}$) and stearic ($C_{18:0}$) acids. The term "FDA saturates" as used herein means this above-defined sum. Unless total saturate content is specified, the saturated fatty acid values expressed here include only "FDA saturates."

All percent fatty acids herein are percent by weight of the oil of which the fatty acid is a component.

As used herein, a "line" is a group of plants that display little or no genetic variation between individuals for at least one trait. Such lines may be created by several generations of self-pollination and selection, or vegetative propagation from a single parent using tissue or cell culture techniques. As used herein, the term "variety" refers to a line which is used for commercial production.

The term "mutagenesis" refers to the use of a mutagenic agent to induce random genetic mutations within a population of individuals. The treated population, or a subsequent generation of that population, is then screened for usable trait(s) that result from the mutations. A "population" is any group of individuals that share a common gene pool. As used herein "$M_0$" is untreated seed. As used herein, "$M_1$" is the seed (and resulting plants) exposed to a mutagenic agent, while "$M_2$" is the progeny (seeds and plants) of self-pollinated $M_1$ plants, "$M_3$" is the progeny of self-pollinated $M_2$ plants, and "$M_4$" is the progeny of self-pollinated $M_3$ plants. "$M_5$" is the progeny of self-pollinated $M_4$ plants. "$M_6$", "$M_7$", etc. are each the progeny of self-pollinated plants of the previous generation. The term "selfed" as used herein means self-pollinated.

"Stability" or "stable" as used herein means that with respect to a given fatty acid component, the component is maintained from generation to generation for at least two generations and preferably at least three generations at substantially the same level, e.g., preferably ±5%. The method of invention is capable of creating lines with improved fatty acid compositions stable up to ±5% from generation to generation. The above stability may be affected by temperature, location, stress and time of planting. Thus, comparison of fatty acid profiles should be made from seeds produced under similar growing conditions. Stability may be measured based on knowledge of prior generation.

Intensive breeding has produced *Brassica* plants whose seed oil contains less than 2% erucic acid. The same varieties have also been bred so that the defatted meal contains less than 30 μmol glucosinolates/gram. "Canola" as used herein refers to plant variety seed or oil which contains less than 2% erucic acid ($C_{22:1}$), and meal with less than 30 μmol glucosinolates/gram.

Applicants have discovered plants with mutations in a delta-12 fatty acid desaturase gene. Such plants have useful alterations in the fatty acid compositions of the seed oil. Such mutations confer, for example, an elevated oleic acid content, a decreased, stabilized linoleic acid content, or both elevated oleic acid and decreased, stabilized linoleic acid content.

Applicants have further discovered plants with mutations in a delta-15 fatty acid desaturase gene. Such plants have useful alterations in the fatty acid composition of the seed oil, e.g., a decreased, stabilized level of α-linolenic acid.

Applicants have further discovered isolated nucleic acid fragments comprising sequences that carry mutations within the coding sequence of delta-12 or delta-15 desaturases. The mutations confer desirable alterations in fatty acid levels in the seed oil of plants carrying such mutations. Delta-12 fatty acid desaturase is also known as omega-6 fatty acid desaturase and is sometimes referred to herein as 12-DES. Delta-15 fatty acid desaturase is also known as omega-3 fatty acid desaturase and is sometimes referred to herein as 15-DES.

A nucleic acid fragment of the invention contains a mutation in a microsomal delta-12 fatty acid desaturase coding sequence or in a microsomal delta-15 fatty acid desaturase coding sequence. Such a mutation renders the resulting desaturase gene product non-functional in plants, relative to the function of the gene product encoded by the wild-type sequence. The non-functionality of the 12-DES gene product can be inferred from the decreased level of reaction product (linoleic acid) and increased level of substrate (oleic acid) in plant tissues expressing the mutant sequence, compared to the corresponding levels in plant tissues expressing the wild-type sequence. The non-functionality of the 15-DES gene product can be inferred from the decreased level of reaction product (α-linolenic acid) and the increased level of substrate (linoleic acid) in plant tissues expressing the mutant sequence, compared to the corresponding levels in plant tissues expressing the wild-type sequence.

A nucleic acid fragment of the invention may comprise a portion of the coding sequence, e.g., at least 20 nucleotides, provided that the fragment contains at least one mutation in the coding sequence. In one embodiment, a nucleic acid fragment of the invention comprises the full length coding sequence of a mutant delta-12 or mutant delta-15 fatty acid desaturase.

A mutation in a nucleic acid fragment of the invention may be in any portion of the coding sequence that renders the resulting gene product non-functional. Suitable types of mutations include, without limitation, insertions of nucleotides, deletions of nucleotides, or transitions and transversions in the wild-type coding sequence. Such mutations result in insertions of one or more amino acids, deletions of one or more amino acids, and non-conservative amino acid substitutions in the corresponding gene product. In some embodiments, the sequence of a nucleic acid fragment may comprise more than one mutation or more than one type of mutation.

Insertion or deletion of amino acids in a coding sequence may, for example, disrupt the conformation of essential alpha-helical or beta-pleated sheet regions of the resulting gene product. Amino acid insertions or deletions may also disrupt binding or catalytic sites important for gene product activity. It is known in the art that the insertion or deletion of a larger number of contiguous amino acids is more likely to render the gene product non-functional, compared to a smaller number of inserted or deleted amino acids.

Non-conservative amino acid substitutions may replace an amino acid of one class with an amino acid of a different class. Non-conservative substitutions may make a substantial change in the charge or hydrophobicity of the gene product. Non-conservative amino acid substitutions may also make a substantial change in the bulk of the residue side chain, e.g., substituting an alanyl residue for a isoleucyl residue.

Examples of non-conservative substitutions include the substitution of a basic amino acid for a non-polar amino acid, or a polar amino acid for an acidic amino acid. Because there are only 20 amino acids encoded in a gene, substitutions that result in a non-functional gene product may be determined by routine experimentation, incorporating amino acids of a different class in the region of the gene product targeted for mutation.

Preferred mutations are in a region of the nucleic acid having an amino acid sequence motif that is conserved among delta-12 fatty acid desaturases or delta-15 fatty acid desaturases, such as a His-Xaa-Xaa-Xaa-His motif (Tables 1-3). An example of a suitable region has a conserved HECGH (SEQ ID NO:9) motif that is found, for example, in nucleotides corresponding to amino acids 105 to 109 of the *Arabidopsis* and *Brassica* delta-12 desaturase sequences, in nucleotides corresponding to amino acids 101 to 105 of the soybean delta-12 desaturase sequence and in nucleotides corresponding to amino acids 111 to 115 of the maize delta-12 desaturase sequence (Table 1). See e.g., WO 94/11516; Okuley et al., Plant Cell 6:147-158 (1994). The one letter amino acid designations used herein are described in Alberts, B. et al., Molecular Biology of the Cell, 3rd edition, Garland Publishing, New York, 1994. Amino acids flanking this motif are also highly conserved among delta-12 and delta-15 desaturases and are also suitable candidates for mutations in fragments of the invention. An illustrative embodiment of a mutation in a nucleic acid fragment of the invention is a Glu to Lys substitution in the HECGH (SEQ ID NO:9) motif of a *Brassica* microsomal delta-12 desaturase sequence, either the D form or the F form. This mutation results in the sequence HECGH (SEQ ID NO:9) being changed to HKCGH (SEQ ID NO:10) as seen by comparing SEQ ID NO:2 (wild-type D form) to SEQ ID NO:4 (mutant D form).

A similar motif may be found at amino acids 101 to 105 of the *Arabidopsis* microsomal delta-15 fatty acid desaturase, as well as in the corresponding rape and soybean desaturases (Table 5). See, e.g., WO 93/11245; Arondel, V. et al., Science, 258:1153-1155 (1992); Yadav, N. et al., Plant Physiol., 103:467-476 (1993). Plastid delta-15 fatty acids have a similar motif (Table 5).

Among the types of mutations in an HECGH (SEQ ID NO:9) motif that render the resulting gene product non-functional are non-conservative substitutions. An illustrative example of a non-conservative substitution is substitution of a glycine residue for either the first or second histidine. Such a substitution replaces a polar residue (histidine) with a non-polar residue (glycine). Another type of mutation that renders the resulting gene product non-functional is an insertion mutation, e.g., insertion of a glycine between the cystine and glutamic acid residues in the HECGH (SEQ ID NO:9) motif.

Other regions having suitable conserved amino acid motifs include the HRRHH (SEQ ID NO:11) motif shown in Table 2 and the HVAHH (SEQ ID NO: 12) motif shown in Table 3. See, e.g., WO 94/11516; Hitz, W. et al., Plant Physiol., 105:635-641 (1994); Okuley, J., et al., supra; and Yadav, N. et al., supra.

Another region suitable for a mutation in a delta-12 desaturase sequence contains the motif KYLNNP (SEQ ID NO: 13) at nucleotides corresponding to amino acids 171 to 175 of the *Brassica* desaturase sequence (Table 4). An illustrative example of a mutation is this region is a Leu to His substitution, resulting in the amino acid sequence KY HNN (SEQ ID NO:14).

TABLE 1

Alignment of Amino Acid Sequences from Microsomal Delta-12 Fatty Acid Desaturases

| Species | Position | Amino Acid Sequence |
| --- | --- | --- |
| *Arabidopsis thaliana* | 100-129 | IWVIAHECGH HAFSDYQWLD DTVGLIFHSF (SEQ ID NO:15) |
| Glycine max | 96-125 | VWVIAHECGH HAFSKYQWVD DVVGLTLHST (SEQ ID NO:16) |
| Zea mays | 106-135 | VWVIAHECGH HAFSDYSLLD DVVGLVLHSS (SEQ ID NO:17) |
| Ricinus communis[a] | 1-29 | WVMAHDCGH HAFSDYQLLD DVVGLILHSC (SEQ ID NO:18) |
| Brassica napus D | 100-128 | VWVIAHECGH HAFSDYQWLD DTVGLIFHS (SEQ ID NO:19) |
| Brassica napus F | 100-128 | VWVIAHECGH HAFSDYQWLD DTVGLIFHS (SEQ ID NO:19) |

[a]from plasmid pRF2-1C

TABLE 2

Alignment of Amino Acid Sequences from Microsomal Delta-12 Fatty Acid Desaturases

| Species | Position | Amino Acid Sequence |
| --- | --- | --- |
| *Arabidopsis thaliana* | 130-158 | LLVPYFSWKY SHRRHHSNTG SLERDEVFV (SEQ ID NO:20) |
| Glycine max | 126-154 | LLVPYFSWKI SHRRHHSNTG SLDRDEVFV (SEQ ID NO:21) |
| Zea mays | 136-164 | LMVPYFSWKY SHRRHHSNTG SLERDEVFV (SEQ ID NO:22) |
| Ricinus communis[a] | 30-58 | LLVPYFSWKH SHRRHHSNTG SLERDEVFV (SEQ ID NO:23) |
| Brassica napus D | 130-158 | LLVPYFSWKY SHRSHHSNTG SLERDEVFV (SEQ ID NO:24) |
| Brassica napus F | 130-158 | LLVPYFSWKY SHRRHHSNTG SLERDEVFV (SEQ ID NO:48) |

[a]from plasmid pRF2-1C

TABLE 3

Alignment of Amino Acid Sequences from Microsomal Delta-12 Fatty Acid Desaturases

| Species | Position | Amino Acid Sequence |
|---|---|---|
| Arabidopsis thaliana | 298-333 | DRDYGILNKV FHNITDTHVA HHLFSTMPHY NAMEAT (SEQ ID NO:25) |
| Glycine max | 294-329 | DRDYGILNKV FHHITDTHVA HHLFSTMPHY HAMEAT (SEQ ID NO:26) |
| Zea mays | 305-340 | DRDYGILNRV FHNITDTHVA HHLFSTMPHY HAMEAT (SEQ ID NO:27) |
| Ricinus communis[a] | 198-224 | DRDYGILNKV FHNITDTQVA HHLF TMP (SEQ ID NO:28) |
| Brassica napus D | 299-334 | DRDYGILNKV FHNITDTHVA HHPFSTMPHY HAMEAT (SEQ ID NO:29) |
| Brassica napus F | 299-334 | DRDYGILNKV FHNITDTHVA HHLFSTMPHY HAMEAT (SEQ ID NO:49) |

[a]from plasmid pRF2-1C

TABLE 4

Alignment of Conserved Amino Acids from Microsomal Delta-12 Fatty Acid Desaturases

| Species | Position Amino Acid Sequence |
|---|---|
| Arabidopsis thaliana | 165-180 IKWYGKYLNN PLGRIM (SEQ ID NO:30) |
| Glycine max | 161-176 VAWFSLYLNN PLGRAV (SEQ ID NO:31) |
| Zea mays | 172-187 PWYTPYVYNN PVGRVV (SEQ ID NO:32) |
| Ricinus communis[a] | 65-80 IRWYSKYLNN PPGRIM (SEQ ID NO:33) |
| Brassica napus D | 165-180 IKWYGKYLNN PLGRTV (SEQ ID NO:34) |
| Brassica napus F | 165-180 IKWYGKYLNN PLGRTV (SEQ ID NO:34) |

[a]from plasmid pRF2-1C

TABLE 5

Alignment of Conserved Amino Acids from Plastid and Microsomal Delta-15 Fatty Acid Desaturases

| Species | Position Amino Acid Sequence |
|---|---|
| Arabidopsis thaliana[a] | 156-177 WALFVLGHD CGHGSFSNDP KLN (SEQ ID NO:35) |
| Brassica napus[a] | 114-135 WALFVLGHD CGHGSFSNDP RLN (SEQ ID NO:36) |
| Glycine max[a] | 164-185 WALFVLGHD CGHGSFSNNS KLN (SEQ ID NO:37) |
| Arabidopsis thaliana | 94-115 WAIFVLGHD CGHGSFSDIP LLN (SEQ ID NO:38) |
| Brassica napus | 85-106 WAIFVLGHD CGHGSFSDIP LLN (SEQ ID NO:38) |
| Glycine max | 93-114 WALFVLGHD CGHGSFSDSP PLN (SEQ ID NO:39) |

[a]Plastid sequences

The conservation of amino acid motifs and their relative positions indicates that regions of a delta-12 or delta-15 fatty acid desaturase that can be mutated in one species to generate a non-functional desaturase can be mutated in the corresponding region from other species to generate a non-functional 12-DES or 15-DES gene product in that species.

Mutations in any of the regions of Tables 1-5 are specifically included within the scope of the invention, provided that such mutation (or mutations) renders the resulting desaturase gene product non-functional, as discussed hereinabove.

A nucleic acid fragment containing a mutant sequence can be generated by techniques known to the skilled artisan. Such techniques include, without limitation, site-directed mutagenesis of wild-type sequences and direct synthesis using automated DNA synthesizers.

A nucleic acid fragment containing a mutant sequence can also be generated by mutagenesis of plant seeds or regenerable plant tissue by, e.g., ethyl methane sulfonate, X-rays or other mutagens. With mutagenesis, mutant plants having the desired fatty acid phenotype in seeds are identified by known techniques and a nucleic acid fragment containing the desired mutation is isolated from genomic DNA or RNA of the mutant line. The site of the specific mutation is then determined by sequencing the coding region of the 12-DES or 15-DES gene. Alternatively, labeled nucleic acid probes that are specific for desired mutational events can be used to rapidly screen a mutagenized population.

Seeds of Westar, a Canadian (*Brassica napus*) spring canola variety, were subjected to chemical mutagenesis. Mutagenized seeds were planted in the greenhouse and the plants were self-pollinated. The progeny plants were individually analyzed for fatty acid composition, and regrown either in the greenhouse or in the field. After four successive generations of self-pollinations, followed by chemical analysis of the seed oil at each cycle, several lines were shown to carry stably inherited mutations in specific fatty acid components, including reduced palmitic acid ($C_{16:0}$), increased palmitic acid, reduced stearic acid ($C_{18:0}$), increased oleic acid ($C_{18:1}$), reduced linoleic acid ($C_{18:2}$) and reduced linolenic acid ($C_{18:3}$), in the seed oil.

The general experimental scheme for developing lines with stable fatty acid mutations is shown in Scheme I hereinafter.

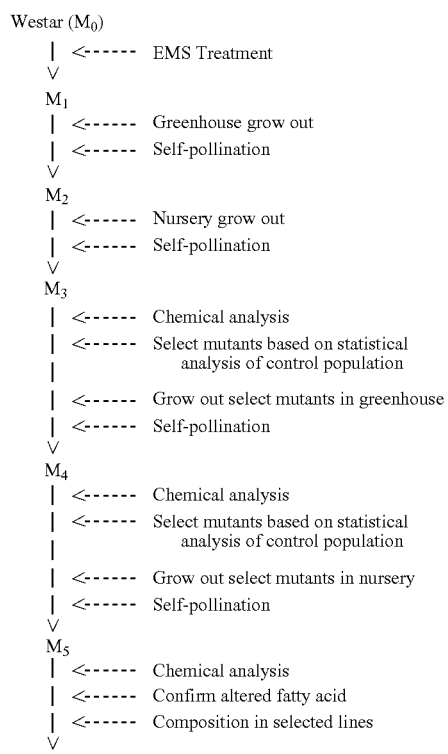

Westar seeds ($M_0$) were mutagenized with ethylmethanesulfonate (EMS). Westar is a registered Canadian spring variety with canola quality. The fatty acid composition of field-grown Westar, 3.9% $C_{16:0}$, 1.9% $C_{18:0}$, 67.5% $C_{18:1}$, 17.6% $C_{18:2}$, 7.4% $C_{18:3}$, <2% $C20:1+C_{22:1}$, has remained stable under commercial production, with <+10% deviation, since 1982. The disclosed method may be applied to all oilseed *Brassica* species, and to both Spring and Winter maturing types within each species. Physical mutagens, including but not limited to X-rays, UV rays, and other physical treatments which cause chromosome damage, and other chemical mutagens, including but not limited to ethidium bromide, nitrosoguanidine, diepoxybutane etc. may also be used to induce mutations. The mutagenesis treatment may also be applied to other stages of plant development, including but not limited to cell cultures, embryos, microspores and shoot apices. The $M_1$ seeds were planted in the greenhouse and $M_1$ plants were individually self-pollinated.

$M_2$ seed was harvested from the greenhouse and planted in the field in a plant-to-row design. Each plot contained six rows, and five $M_2$ lines were planted in each plot. Every other plot contained a row of non-mutagenized Westar as a control. Based on gas chromatographic analysis of $M_2$ seed, those lines which had altered fatty acid composition were self-pollinated and individually harvested.

$M_3$ seeds were evaluated for mutations on the basis of a Z-distribution. An extremely stringent 1 in 10,000 rejection rate was employed to establish statistical thresholds to distinguish mutation events from existing variation. Mean and standard deviation values were determined from the non-mutagenized Westar control population in the field. The upper and lower statistical thresholds for each fatty acid were determined from the mean value of the population±the standard deviation, multiplied by the Z-distribution. Based on a population size of 10,000, the confidence interval is 99.99%.

Seeds ($M_3$) from those $M_2$ lines which exceeded either the upper or lower statistical thresholds were replanted in the greenhouse and self-pollinated. This planting also included Westar controls. The $M_4$ seed was re-analyzed using new statistical thresholds established with a new control population. Those $M_4$ lines which exceeded the new statistical thresholds for selected fatty acid compositions were advanced to the nursery. Following self-pollination, $M_5$ seed from the field were re-analyzed once again for fatty acid composition. Those lines which remained stable for the selected fatty acids were considered stable mutations.

"Stable mutations" as used herein are defined as $M_5$ or more advanced lines which maintain a selected altered fatty acid profile for a minimum of three generations, including a minimum of two generations under field conditions, and exceeding established statistical thresholds for a minimum of two generations, as determined by gas chromatographic analysis of a minimum of 10 randomly selected seeds bulked together. Alternatively, stability may be measured in the same way by comparing to subsequent generations. In subsequent generations, stability is defined as having similar fatty acid profiles in the seed as that of the prior or subsequent generation when grown under substantially similar conditions.

The amount of variability for fatty acid content in a seed population is quite significant when single seeds are analyzed. Randomly selected single seeds and a ten seed bulk sample of a commercial variety were compared. Significant variation among the single seeds was detected (Table A). The half-seed technique (Downey, R. K. and B. L. Harvey, Can. J. Plant Sci., 43:271 [1963]) in which one cotyledon of the germinating seed is analyzed for fatty acid composition and the remaining embryo grown into a plant has been very useful to plant breeding work to select individuals in a population for further generation analysis. The large variation seen in the single seed analysis (Table A) is reflected in the half-seed technique.

TABLE A

Single Seed Analysis for Fatty Acid Composition[1]

| SAMPLE | 16:0 | 16:1 | 18:0 | 18:1 | 18:2 | 18:3 | 20:0 | 20:1 | 22:0 | 22:1 |
|---|---|---|---|---|---|---|---|---|---|---|
| Bulk | 3.2 | 0.4 | 1.8 | 20.7 | 13.7 | 9.8 | 0.8 | 11.2 | 0.4 | 32.2 |
| 1 | 2.8 | 0.2 | 1.1 | 14.6 | 14.6 | 11.1 | 0.8 | 9.8 | 0.7 | 38.2 |
| 2 | 3.3 | 0.2 | 1.3 | 13.1 | 14.4 | 11.7 | 0.9 | 10.5 | 0.7 | 37.0 |
| 3 | 3.0 | — | 1.2 | 12.7 | 15.3 | 10.6 | 0.8 | 7.3 | 0.7 | 43.2 |
| 4 | 2.8 | 0.2 | 1.1 | 16.7 | 13.2 | 9.1 | 0.8 | 11.2 | 0.4 | 38.9 |
| 5 | 3.0 | — | 1.8 | 15.2 | 13.3 | 8.4 | 1.3 | 8.7 | 0.9 | 42.3 |
| 6 | 3.1 | — | 1.3 | 14.4 | 14.6 | 10.3 | 1.0 | 10.9 | 0.8 | 39.3 |
| 7 | 2.6 | — | 1.2 | 15.7 | 13.8 | 9.9 | 0.9 | 12.2 | 0.5 | 37.0 |
| 8 | 3.1 | — | 1.1 | 16.2 | 13.4 | 10.6 | 0.6 | 9.2 | 0.8 | 41.4 |
| 9 | 2.7 | 0.1 | 1.0 | 13.5 | 11.2 | 11.3 | 0.8 | 6.2 | 0.7 | 46.9 |
| 10 | 3.4 | 0.2 | 1.4 | 13.9 | 17.5 | 10.8 | 1.1 | 10.0 | 0.9 | 36.2 |
| 11 | 2.8 | 0.2 | 1.2 | 12.7 | 12.9 | 10.3 | 1.0 | 7.9 | 0.9 | 43.3 |
| 12 | 2.3 | 0.1 | 1.6 | 20.7 | 14.8 | 6.5 | 1.1 | 12.5 | 0.8 | 34.5 |
| 13 | 2.6 | 0.2 | 1.3 | 21.0 | 11.4 | 7.6 | 1.0 | 11.6 | 0.6 | 36.7 |
| 14 | 2.6 | 0.1 | 1.2 | 14.7 | 13.2 | 9.4 | 0.9 | 10.1 | 0.8 | 40.8 |
| 15 | 2.9 | 0.2 | 1.4 | 16.6 | 15.1 | 11.2 | 0.7 | 9.1 | 0.3 | 36.1 |
| 16 | 3.0 | 0.2 | 1.1 | 12.4 | 13.7 | 10.4 | 0.9 | 8.7 | 0.8 | 42.7 |
| 17 | 2.9 | 0.1 | 1.1 | 21.1 | 12.3 | 7.1 | 0.8 | 12.4 | 0.5 | 36.8 |
| 18 | 3.1 | 0.1 | 1.2 | 13.7 | 13.1 | 10.4 | 1.0 | 8.8 | 0.7 | 41.6 |
| 19 | 2.7 | 0.1 | 1.0 | 11.1 | 13.4 | 11.7 | 0.8 | 7.9 | 0.8 | 43.5 |
| 20 | 2.3 | 0.2 | 0.2 | 18.2 | 13.9 | 8.2 | 0.9 | 10.3 | 0.8 | 38.2 |
| Average | 2.8 | 0.2 | 1.2 | 15.4 | 13.8 | 9.8 | 0.9 | 9.8 | 0.7 | 39.7 |
| Minimum | 2.3 | 0.1 | 0.2 | 11.1 | 11.2 | 6.5 | 0.6 | 6.2 | 0.3 | 34.5 |
| Maximum | 3.4 | 0.2 | 1.8 | 21.1 | 17.5 | 11.7 | 1.3 | 12.5 | 0.9 | 46.9 |
| Range | 1.1 | 0.1 | 1.6 | 9.9 | 6.3 | 5.3 | 0.7 | 6.4 | 0.6 | 12.4 |

[1]Values expressed as percent of total oil

Plant breeders using the half-seed technique have found it unreliable in selecting stable genetically controlled fatty acid mutations (Stefanson, B. R., In; High and Low Erucic Acid Rapeseed Oils, Ed. N. T. Kenthies, Academic Press, Inc., Canada (1983) pp. 145-159). Although valuable in selecting individuals from a population, the selected traits are not always transmitted to subsequent generations (Rakow, G. and McGregor, D. I., J. Amer. Oil Chem. Soc. (1973) 50:400-403. To determine the genetic stability of the selected plants several self-pollinated generations are required (Robelen, G. In: Biotechnology for the Oils and Fats Industry, Ed. C. Ratledge, P. Dawson and J. Rattray, American Oil Chemists Society (1984) pp. 97-105) with chemical analysis of a bulk seed sample.

Mutation breeding has traditionally produced plants carrying, in addition to the trait of interest, multiple, deleterious traits, e.g., reduced plant vigor and reduced fertility. Such traits may indirectly affect fatty acid composition, producing an unstable mutation; and/or reduce yield, thereby reducing the commercial utility of the invention. To eliminate the occurrence of deleterious mutations and reduce the load of mutations carried by the plant a low mutagen dose was used in the seed treatments to create an LD30 population. This allowed for the rapid selection of single gene mutations for fatty acid traits in agronomic backgrounds which produce acceptable yields.

Other than changes in the fatty acid composition of the seed oil, the mutant lines described here have normal plant phenotype when grown under field conditions, and are commercially useful. "Commercial utility" is defined as having a yield, as measured by total pounds of seed or oil produced per acre, within 15% of the average yield of the starting ($M_0$) canola variety grown in the same region. To be commercially useful, plant vigor and high fertility are such that the crop can be produced in this yield by farmers using conventional farming equipment, and the oil with altered fatty acid composition can be extracted using conventional crushing and extraction equipment.

The seeds of several different fatty acid lines have been deposited with the American Type Culture Collection and have the following accession numbers.

| Line | Accession No. | Deposit Date |
|---|---|---|
| A129.5 | 40811 | May 25, 1990 |
| A133.1 | 40812 | May 25, 1990 |
| A144.1 | 40813 | May 25, 1990 |
| A200.7 | 40816 | May 31, 1990 |
| M3032.1 | 75021 | Jun. 7, 1991 |
| M3094.4 | 75023 | Jun. 7, 1991 |
| M3052.6 | 75024 | Jun. 7, 1991 |
| M3007.4 | 75022 | Jun. 7, 1991 |
| M3062.8 | 75025 | Jun. 7, 1991 |
| M3028.10 | 75026 | Jun. 7, 1991 |
| IMC130 | 75446 | Apr. 16, 1993 |

In some plant species or varieties more than one form of endogenous microsomal delta-12 desaturase may be found. In amphidiploids, each form may be derived from one of the parent genomes making up the species under consideration. Plants with mutations in both forms have a fatty acid profile that differs from plants with a mutation in only one form. An example of such a plant is Brassica napus line Q508, a doubly mutagenized line containing a mutant D-form of a wild-type delta-12 desaturase (SEQ ID NO: 1) and a mutant F-form of a wild-type delta-12 desaturase (SEQ ID NO:5).

Preferred host or recipient organisms for introduction of a nucleic acid fragment of the invention are the oil-producing species, such as soybean (Glycine max), rapeseed (e.g., Brassica napus, B. rapa and B. juncea), sunflower (Helianthus annus), castor bean (Ricinus communis), corn (Zea mays), and safflower (Carthamus tinctorius).

Plants according to the invention preferably contain an altered fatty acid profile. For example, oil obtained from seeds of such plants may have from about 69 to about 90% oleic acid, based on the total fatty acid composition of the seed. Such oil preferably has from about 74 to about 90% oleic acid, more preferably from about 80 to about 90% oleic acid. In some embodiments, oil obtained from seeds produced by plants of the invention may have from about 2.0% to about 5.0% saturated fatty acids, based on total fatty acid composition of the seeds. In some embodiments, oil obtained from seeds of the invention may be from about 1.0% to about 10.0% linoleic acid, or from about 0.5% to about 10.0% α-linolenic acid.

In one embodiment of the claimed invention, a plant contains both a 12-DES mutation and a 15-DES mutation. Such plants can have a fatty acid composition comprising very high oleic acid and very low alpha-linolenic acid levels. Mutations in 12-DES and 15-DES may be combined in a plant by making a genetic cross between 12-DES and 15-DES single mutant lines. A plant having a mutation in delta-12 fatty acid desaturase is crossed or mated with a second plant having a mutation in delta-15 fatty acid desaturase. Seeds produced from the cross are planted and the resulting plants are selfed in order to obtain progeny seeds. These progeny seeds are then screened in order to identify those seeds carrying both mutant genes.

Alternatively, a line possessing either a 12-DES or a 15-DES mutation can be subjected to mutagenesis to generate a plant or plant line having mutations in both 12-DES and 15-DES. For example, the IMC129 line has a mutation in the coding region ($Glu_{106}$ to $Lys_{106}$) of the D form of the microsomal delta-12 desaturase structural gene. Cells (e.g., seeds) of this line can be mutagenized to induce a mutation in a 15-DES gene, resulting in a plant or plant line carrying a mutation in a delta-12 fatty acid desaturase gene and a mutation in a delta-15 fatty acid desaturase gene.

Progeny includes descendants of a particular plant or plant line, e.g., seeds developed on an instant plant. Progeny of an instant plant include seeds formed on $F_1$, $F_2$, $F_3$, and subsequent generation plants, or seeds formed on $BC_1$, $BC_2$, $BC_3$ and subsequent generation plants.

Those seeds having an altered fatty acid composition may be identified by techniques known to the skilled artisan, e.g., gas-liquid chromatography (GLC) analysis of a bulked seed sample or of a single half-seed. Half-seed analysis is well known in the art to be useful because the viability of the embryo is maintained and thus those seeds having a desired fatty acid profile may be planted to from the next generation. However, half-seed analysis is also known to be an inaccurate representation of genotype of the seed being analyzed. Bulk seed analysis typically yields a more accurate representation of the fatty acid profile of a given genotype.

The nucleic acid fragments of the invention can be used as markers in plant genetic mapping and plant breeding programs. Such markers may include restriction fragment length polymorphism (RFLP), random amplification polymorphism detection (RAPD), polymerase chain reaction (PCR) or self-sustained sequence replication (3SR) markers, for example. Marker-assisted breeding techniques may be used to identify and follow a desired fatty acid composition during the breeding process. Marker-assisted breeding techniques may be used in addition to, or as an alternative to, other sorts of identification techniques. An example of marker-assisted breeding is the use of PCR primers that specifically amplify a sequence containing a desired mutation in 12-DES or 15-DES.

Methods according to the invention are useful in that the resulting plants and plant lines have desirable seed fatty acid compositions as well as superior agronomic properties compared to known lines having altered seed fatty acid composition. Superior agronomic characteristics include, for example, increased seed germination percentage, increased seedling vigor, increased resistance to seedling fungal diseases (damping off, root rot and the like), increased yield, and improved standability.

While the invention is susceptible to various modifications and alternative forms, certain specific embodiments thereof are described in the general methods and examples set forth below. For example the invention may be applied to all Brassica species, including B. rapa, B. juncea, and B. hirta, to produce substantially similar results. It should be understood, however, that these examples are not intended to limit the invention to the particular forms disclosed but, instead the invention is to cover all modifications, equivalents and alternatives falling within the scope of the invention. This includes the use of somaclonal variation; physical or chemical mutagenesis of plant parts; anther, microspore or ovary culture followed by chromosome doubling; or self- or cross-pollination to transmit the fatty acid trait, alone or in combination with other traits, to develop new Brassica lines.

EXAMPLE 1

Selection of Low FDA Saturates

Prior to mutagenesis, 30,000 seeds of B. napus cv. Westar seeds were preimbibed in 300-seed lots for two hours on wet filter paper to soften the seed coat. The preimbibed seeds were placed in 80 mM ethylmethanesulfonate (EMS) for four hours. Following mutagenesis, the seeds were rinsed three times in distilled water. The seeds were sown in 48-well flats containing Pro-Mix. Sixty-eight percent of the mutagenized seed germinated. The plants were maintained at 25° C./15° C., 14/10 hr day/night conditions in the greenhouse. At flowering, each plant was individually self-pollinated.

$M_2$ seed from individual plants were individually catalogued and stored, approximately 15,000 $M_2$ lines was planted in a summer nursery in Carman, Manitoba. The seed from each selfed plant were planted in 3-meter rows with 6-inch row spacing. Westar was planted as the check variety. Selected lines in the field were selfed by bagging the main raceme of each plant. At maturity, the selfed plants were individually harvested and seeds were catalogued and stored to ensure that the source of the seed was known.

Self-pollinated $M_3$ seed and Westar controls were analyzed in 10-seed bulk samples for fatty acid composition via gas chromatography. Statistical thresholds for each fatty acid component were established using a Z-distribution with a stringency level of 1 in 10,000. The selected $M_3$ seeds were planted in the greenhouse along with Westar controls. The seed was sown in 4-inch pots containing Pro-Mix soil and the plants were maintained at 25° C./15° C., 14/10 hr day/night cycle in the greenhouse. At flowering, the terminal raceme was self-pollinated by bagging. At maturity, selfed $M_4$ seed was individually harvested from each plant, labelled, and stored to ensure that the source of the seed was known.

The $M_4$ seed was analyzed in 10-seed bulk samples. Statistical thresholds for each fatty acid component were established from 259 control samples using a Z-distribution of 1 in 800. Selected $M_4$ lines were planted in a field trial in Carman, Manitoba in 3-meter rows with 6-inch spacing. Ten $M_4$ plants in each row were bagged for self-pollination. At maturity, the selfed plants were individually harvested and the open pollinated plants in the row were bulk harvested. The $M_5$ seed from single plant selections was analyzed in 10-seed bulk samples and the bulk row harvest in 50-seed bulk samples.

Selected $M_5$ lines were planted in the greenhouse along with Westar controls. The seed was grown as previously described. At flowering the terminal raceme was self-pollinated by bagging. At maturity, selfed $M_6$ seed was individually harvested from each plant and analyzed in 10-seed bulk samples for fatty acid composition.

Selected $M_6$ lines were entered into field trials in Eastern Idaho. The four trial locations were selected for the wide variability in growing conditions. The locations included Burley, Tetonia, Lamont and Shelley (Table I). The lines were planted in four 3-meter rows with an 8-inch spacing, each plot was replicated four times. The planting design was determined using a Randomized Complete Block Designed. The commercial cultivar Westar was used as a check cultivar. At maturity the plots were harvested to determine yield. Yield of the entries in the trial was determined by taking the statistical average of the four replications. The Least Significant Difference Test was used to rank the entries in the randomized complete block design.

TABLE I

Trial Locations for Selected Fatty Acid Mutants

| LOCATION | SITE CHARACTERIZATIONS |
|---|---|
| BURLEY | Irrigated. Long season. High temperatures during flowering. |
| TETONIA | Dryland. Short season. Cool temperatures. |
| LAMONT | Dryland. Short season. Cool temperatures. |
| SHELLEY | Irrigated. Medium season. High temperatures during flowering. |

To determine the fatty acid profile of entries, plants in each plot were bagged for self-pollination. The $M_7$ seed from single plants was analyzed for fatty acids in ten-seed bulk samples.

To determine the genetic relationships of the selected fatty acid mutants crosses were made. Flowers of $M_6$ or later generation mutations were used in crossing. $F_1$ seed was harvested and analyzed for fatty acid composition to determine the mode of gene action. The $F_1$ progeny were planted in the greenhouse. The resulting plants were self-pollinated, the $F_2$ seed harvested and analyzed for fatty acid composition for allelism studies. The $F_2$ seed and parent line seed was planted in the greenhouse, individual plants were self-pollinated. The $F_3$ seed of individual plants was tested for fatty acid composition using 10-seed bulk samples as described previously.

In the analysis of some genetic relationships dihaploid populations were made from the microspores of the $F_1$ hybrids. Self-pollinated seed from dihaploid plants were analyzed for fatty acid analysis using methods described previously.

For chemical analysis, 10-seed bulk samples were hand ground with a glass rod in a 15-mL polypropylene tube and extracted in 1.2 mL 0.25 N KOH in 1:1 ether/methanol. The sample was vortexed for 30 sec. and heated for 60 sec. in a 60° C. water bath. Four mL of saturated NaCl and 2.4 mL of iso-octane were added, and the mixture was vortexed again. After phase separation, 600 μL of the upper organic phase were pipetted into individual vials and stored under nitrogen at −5° C. One μL samples were injected into a Supelco SP-2330 fused silica capillary column (0.25 mm ID, 30 M length, 0.20 μm df).

The gas chromatograph was set at 180° C. for 5.5 minutes, then programmed for a 2° C./minute increase to 212° C., and held at this temperature for 1.5 minutes. Total run time was 23 minutes. Chromatography settings were: Column head pressure—15 psi, Column flow (He)—0.7 mL/min., Auxiliary and Column flow—33 mL/min., Hydrogen flow—33 mL/min., Air flow—400 mL/min., Injector temperature—250° C., Detector temperature - 300° C., Split vent—1/15.

Table II describes the upper and lower statistical thresholds for each fatty acid of interest.

TABLE II

Statistical Thresholds for Specific Fatty Acids Derived from Control Westar Plantings

| Genotype | Percent Fatty Acids | | | | | |
|---|---|---|---|---|---|---|
| | $C_{16:0}$ | $C_{18:0}$ | $C_{18:1}$ | $C_{18:2}$ | $C_{18:3}$ | Sats* |
| $M_3$ Generation (1 in 10,000 rejection rate) | | | | | | |
| Lower | 3.3 | 1.4 | — | 13.2 | 5.3 | 6.0 |
| Upper | 4.3 | 2.5 | 71.0 | 21.6 | 9.9 | 8.3 |
| $M_4$ Generation (1 in 800 rejection rate) | | | | | | |
| Lower | 3.6 | 0.8 | — | 12.2 | 3.2 | 5.3 |
| Upper | 6.3 | 3.1 | 76.0 | 32.4 | 9.9 | 11.2 |
| $M_5$ Generation (1 in 755 rejection rate) | | | | | | |
| Lower | 2.7 | 0.9 | — | 9.6 | 2.6 | 4.5 |
| Upper | 5.7 | 2.7 | 80.3 | 26.7 | 9.6 | 10.0 |

*Sats = Total Saturate Content

At the $M_3$ generation, twelve lines exceeded the lower statistical threshold for palmitic acid (≦3.3%). Line W13097.4 had 3.1% palmitic acid and an FDA saturate content of 4.5%. After a cycle in the greenhouse, $M_4$ seed from line W13097.4 (designated line A144) was analyzed. Line W13097.4.1(A144.1) had 3.1% $C_{16:0}$, exceeding the lower statistical threshold of 3.6%. The FDA saturate content for A144.1 was 4.5%. The fatty acid compositions for the $M_3$, $M_4$ and $M_5$ generations of this family are summarized in Table III.

TABLE III

Fatty Acid Composition of a Low Palmitic Acid/Low FDA Saturate Canola Line Produced by Seed Mutagenesis

| Genotype[a] | Percent Fatty Acids | | | | | | |
|---|---|---|---|---|---|---|---|
| | $C_{16:0}$ | $C_{18:0}$ | $C_{18:1}$ | $C_{18:2}$ | $C_{18:3}$ | Sats[b] | Tot Sat[c] |
| Westar | 3.9 | 1.9 | 67.5 | 17.6 | 7.4 | 5.9 | 7.0 |
| W13097.4 ($M_3$) | 3.1 | 1.4 | 63.9 | 18.6 | 9.5 | 4.5 | 5.6 |
| W13097.4 ($M_4$) | 3.1 | 1.4 | 66.2 | 19.9 | 6.0 | 4.5 | 5.5 |
| A144.1.9 ($M_5$) | 2.9 | 1.4 | 64.3 | 20.7 | 7.3 | 4.4 | 5.3 |

[a] Letter and numbers up to second decimal point indicate the plant line. Number after second decimal point indicates an individual plant.
[b] Sat = FDA Saturates
[c] Tot Sat = Total Saturate Content The $M_5$ seed of ten self-pollinated A144.1 (ATCC 40813) plants averaged 3.1% palmitic acid and 4.7% FDA saturates. One selfed plant (A144.1.9) contained 2.9% palmitic acid and FDA saturates of 4.4%. Bulk seed analysis from open-pollinated (A144.1) plants at the $M_5$ generation averaged 3.1% palmitic acid and 4.7% FDA saturates. The fatty acid composition of the bulked and individual A144.1 lines are summarized in Table IV.

TABLE IV

Fatty Acid Composition of A144 Low Palmitic Acid/Low FDA Saturate Line

| Genotype[a] | Percent Fatty Acids | | | | | | |
|---|---|---|---|---|---|---|---|
| | $C_{16:0}$ | $C_{18:0}$ | $C_{18:1}$ | $C_{18:2}$ | $C_{18:3}$ | Sats[b] | Tot Sat[c] |
| Individually Self-Pollinated Plants | | | | | | | |
| A144.1.1 | 3.2 | 1.6 | 64.4 | 20.5 | 7.0 | 4.8 | 5.9 |
| A144.1.2 | 3.0 | 1.5 | 67.4 | 18.6 | 6.3 | 4.5 | 5.7 |
| A144.1.3 | 3.6 | 1.8 | 61.4 | 22.4 | 7.5 | 5.2 | 6.6 |
| A144.1.4 | 3.2 | 1.5 | 64.6 | 20.9 | 6.7 | 4.7 | 5.8 |
| A144.1.5 | 3.3 | 1.7 | 60.0 | 23.9 | 7.9 | 5.0 | 6.1 |
| A144.1.6 | 3.1 | 1.4 | 67.3 | 17.8 | 6.5 | 4.6 | 5.2 |
| A144.1.7 | 3.1 | 1.6 | 67.7 | 17.4 | 6.5 | 4.8 | 5.4 |
| A144.1.8 | 3.1 | 1.8 | 66.9 | 18.7 | 6.1 | 4.9 | 5.4 |
| A144.1.9 | 2.9 | 1.4 | 64.3 | 20.7 | 7.3 | 4.4 | 5.3 |
| A144.1.10 | 3.1 | 1.5 | 62.5 | 20.4 | 7.7 | 4.6 | 5.6 |
| Average of Individually Self-Pollinated Plants | | | | | | | |
| A144.1.1-10 | 3.1 | 1.6 | 64.8 | 20.1 | 6.9 | 4.7 | 5.7 |
| Bulk Analysis of Open-Pollinated Plants | | | | | | | |
| A144.1B | 3.1 | 1.6 | 64.8 | 19.4 | 7.8 | 4.7 | 5.7 |

[a] Letter and numbers up to second decimal point indicate the plant line. Number after second decimal point indicates an individual plant.
[b] Sat = FDA Saturates
[c] Tot Sat = Total Saturate Content These reduced levels have remained stable to the $M_7$ generations in both greenhouse and field conditions. These reduced levels have remained stable to the $M_7$ generation in multiple location field trails. Over all locations, the self-pollinated plants (A144) averaged 2.9% palmitic acid and FDA saturates of 4.6%. The fatty acid composition of the A144 lines for each Idaho location are summarized in Table V. In the multiple location replicated trial the yield of A144 was not significantly different in yield from the parent cultivar Westar. By means of seed mutagenesis, the level of saturated fatty acids of canola (B. napus) was reduced from 5.9% to 4.6%. The palmitic acid content was reduced from 3.9% to 2.9%.

TABLE V

Fatty Acid Composition of a Mutant Low Palmitic
Acid/Low FDA Saturate Canola Line at
Different Field Locations in Idaho

| Trial Location | Percent Fatty Acid | | | | | | |
|---|---|---|---|---|---|---|---|
| | $C_{16:0}$ | $C_{18:0}$ | $C_{18:1}$ | $C_{18:2}$ | $C_{18:3}$ | Sats | Tot Sats |
| Burley | 2.9 | 1.3 | 62.3 | 20.6 | 10.3 | 4.2 | 5.0 |
| Tetonia | 2.9 | 1.7 | 59.7 | 21.0 | 11.2 | 4.6 | 5.7 |
| Lamont | 3.1 | 1.8 | 63.2 | 19.5 | 9.0 | 4.9 | 5.9 |
| Shelley | 2.8 | 1.9 | 64.5 | 18.8 | 8.8 | 4.7 | 5.9 |

To determine the genetic relationship of the palmitic acid mutation in A144 ($C_{16:0}$—3.0%, $C_{18:0}$—1.5%, $C_{18:1}$—67.4%, $C_{18:2}$—18.6%, $C_{18:3}$—6.3%) to other fatty acid mutations it was crossed to A129 a mutant high oleic acid ($C_{16:0}$—3.8%, $C_{18:0}$—2.3%, $C_{18:1}$—75.6%, $C_{18:2}$—9.5%, $C_{18:3}$—4.9%). Over 570 dihaploid progeny produced from the $F_1$ hybrid were harvested and analyzed for fatty acid composition. The results of the progeny analysis are summarized in Table VB. Independent segregation of the palmitic traits was observed which demonstrates that the genetic control of palmitic acid in A144 is different from the high oleic acid mutation in A129.

TABLE VB

Genetic Studies of Dihaploid Progeny of A144 × A129

| Genotype | $C_{16:0}$ Content(%) | Frequency Observed | Expected |
|---|---|---|---|
| p − p − p2 − p2 − | 3.0% | 162 | 143 |
| p + p + p2 − p2 − | 3.4% | 236 | 286 |
| p + p + p2 + p2 + | 3.8% | 175 | 143 |

EXAMPLE 2

An additional low FDA saturate line, designated A149.3 (ATCC 40814), was also produced by the method of Example 1. A 50-seed bulk analysis of this line showed the following fatty acid composition: $C_{16:0}$—3.6%, $C_{18:0}$—1.4%, $C_{18:1}$—65.5%, $C_{18:2}$—18.3%, $C_{18:3}$—8.2%, FDA Sats—5.0%, Total Sats—5.9%. This line has also stably maintained its mutant fatty acid composition to the $M_5$ generation. In a multiple location replicated trial the yield of A149 was not significantly different in yield from the parent cultivar Westar.

EXAMPLE 3

An additional low palmitic acid and low FDA saturate line, designated M3094.4 (ATCC 75023), was also produced by the method of Example 1. A 10-seed bulk analysis of this line showed the following fatty acid composition: $C_{16:0}$—2.7%, $C_{18:0}$—1.6%, $C_{18:1}$—66.6%, $C_{18:2}$—20.0%, $C_{18:3}$—6.1%, $C_{20:1}$—1.4%, $C_{22:1}$—0.0%, FDA Saturate —4.3%, Total Saturates —5.2%. This line has stably maintained its mutant fatty acid composition to the $M_5$ generation. In a single replicated trial the yield of M3094 was not significantly different in yield from the parent cultivar.

M3094.4 was crossed to A144, a low palmitic acid mutation (Example 1) for allelism studies. Fatty acid composition of the $F_2$ seed showed the two lines to be allelic. The mutational events in A144 and M3094, although different in origin, are in the same gene.

EXAMPLE 4

In the studies of Example 1, at the $M_3$ generation, 470 lines exceed the upper statistical threshold for palmitic acid (>4.3%). One $M_3$ line, W14538.6, contained 9.2% palmitic acid. Selfed progenies of this line, since designated M3007.4 (ATCC 75022), continued to exceed to the upper statistical threshold for high palmitic acid at both the $M_4$ and $M_5$ generations with palmitic acid levels of 11.7% and 9.1%, respectively. The fatty acid composition of this high palmitic acid mutant, which was stable to the $M_7$ generation under both field and greenhouse conditions, is summarized in Table VI.

TABLE VI

Fatty Acid Composition of a High Palmitic
Acid Canola Line Produced by Seed Mutagenesis

| Genotype | Percent Fatty Acids | | | | | |
|---|---|---|---|---|---|---|
| | $C_{16:0}$ | $C_{18:0}$ | $C_{18:1}$ | $C_{18:2}$ | $C_{18:3}$ | Sats* |
| Westar | 3.9 | 1.9 | 67.5 | 17.6 | 7.4 | 7.0 |
| W114538.6 ($M_3$) | 8.6 | 1.6 | 56.4 | 20.3 | 9.5 | 10.2 |
| M3007.2 ($M_4$) | 11.7 | 2.1 | 57.2 | 18.2 | 5.1 | 13.9 |
| M3007.4 ($M_5$) | 9.1 | 1.4 | 63.3 | 13.7 | 5.5 | 12.7 |

*Sats = Total Saturate Content

To determine the genetic relationship of the high palmitic mutation in M3007.4 to the low palmitic mutation in A144 (Example 1) crosses were made. The $F_2$ progeny were analyzed for fatty acid composition. The data presented in Table VIB shows the high palmitic group ($C_{16}$:0>7.0%) makes up one-quarter of the total population analyzed. The high palmitic acid mutation was controlled by one single gene mutation.

TABLE VIB

Genetic Studies of M3007 × A144

| Genotype | $C_{16:0}$ Content(%) | Frequency Observed | Expected |
|---|---|---|---|
| p − p −/p − hp − | <7.0 | 151 | 142 |
| hp − hp − | >7.0 | 39 | 47 |

An additional $M_3$ line, W4773.7, contained 4.5% palmitic acid. Selfed progenies of this line, since designated A200.7 (ATCC 40816), continued to exceed the upper statistical threshold for high palmitic acid in both the $M_4$ and $M_5$ generations with palmitic acid levels of 6.3% and 6.0%, respectively. The fatty acid composition of this high palmitic acid mutant, which was stable to the $M_7$ generation under both field and greenhouse conditions, is summarized in Table VII.

TABLE VII

Fatty Acid Composition of a High Palmitic
Acid Canola Line Produced by Seed Mutagenesis

| | Percent Fatty Acids | | | | | |
|---|---|---|---|---|---|---|
| Genotype | $C_{16:0}$ | $C_{18:0}$ | $C_{18:1}$ | $C_{18:2}$ | $C_{18:3}$ | Sats* |
| Westar | 3.9 | 1.9 | 67.5 | 17.6 | 7.4 | 7.0 |
| W4773.7 ($M_3$) | 4.5 | 2.9 | 63.5 | 19.9 | 7.1 | 9.3 |
| M4773.7.7 ($M_4$) | 6.3 | 2.6 | 59.3 | 20.5 | 5.6 | 10.8 |
| A200.7.7 ($M_5$) | 6.0 | 1.9 | 60.2 | 20.4 | 7.3 | 9.4 |

*Sats = Total Saturate Content

EXAMPLE 5

Selection of Low Stearic Acid Canola Lines

In the studies of Example 1, at the $M_3$ generation, 42 lines exceeded the lower statistical threshold for stearic acid (<1.4%). Line W14859.6 had 1.3% stearic acid. At the $M_5$ generation, its selfed progeny (M3052.1) continued to fall within the lower statistical threshold for $C_{18:0}$ with 0.8% stearic acid. The fatty acid composition of this low stearic acid mutant, which was stable under both field and greenhouse conditions is summarized in Table VIII. In a single location replicated yield trial M3052.1 was not significantly different in yield from the parent cultivar Westar.

TABLE VIII

Fatty Acid Composition of a Low
Stearic Acid Canola Line Produced by Seed Mutagenesis

| | Percent Fatty Acids | | | | | |
|---|---|---|---|---|---|---|
| Genotype | $C_{16:0}$ | $C_{18:0}$ | $C_{18:1}$ | $C_{18:2}$ | $C_{18:3}$ | Sats |
| Westar | 3.9 | 1.9 | 67.5 | 17.6 | 7.4 | 5.9 |
| W14859.6 ($M_3$) | 5.3 | 1.3 | 56.1 | 23.7 | 9.6 | 7.5 |
| M3052.1 ($M_4$) | 4.9 | 0.9 | 58.9 | 22.7 | 9.3 | 5.8 |
| M3052.6 ($M_5$) | 4.4 | 0.8 | 62.1 | 21.2 | 7.9 | 5.2 |

To determine the genetic relationship of the low stearic acid mutation of M3052.1 to other fatty acid mutations it was crossed to the low palmitic acid mutation A144 (Example 1). Seed from over 300 dihaploid progeny were harvested and analyzed for fatty acid composition. The results are summarized in Table VIIIB. Independent segregation of the palmitic acid and stearic acid traits was observed. The low stearic acid mutation was genetically different from the low palmitic acid mutations found in A144 and M3094.

TABLE VIIIB

Genetic Studies of M3052 × A144

| | | Frequency | |
|---|---|---|---|
| Genotype | $C_{16:0} + C_{18:0}$ Content(%) | Observed | Expected |
| p − p − s − s − | <4.9% | 87 | 77 |
| p − p − s − s −/p + p + s − s − | 4.0% < X < 5.6% | 152 | 154 |
| p + p + s + s + | >5.6% | 70 | 77 |

An additional $M_5$ line, M3051.10, contained 0.9% and 1.1% stearic acid in the greenhouse and field respectively. A ten-seed analysis of this line showed the following fatty acid composition: $C_{16:0}$—3.9%, $C_{18:0}$—1.1%, $C_{18:1}$—61.7%, $C_{18:2}$—23.0%, $C_{18:3}$—7.6%, FDA saturates—5.0%, Total Saturates—5.8%. In a single location replicated yield trial M3051.10 was not significantly different in yield from the parent cultivar Westar. M3051.10 was crossed to M3052.1 for allelism studies. Fatty acid composition of the $F_2$ seed showed the two lines to be allelic. The mutational events in M3051.10 and M3052.1 although different in origin were in the same gene.

An additional $M_5$ line, M3054.7, contained 1.0% and 1.3% stearic acid in the greenhouse and field respectively. A ten-seed analysis of this line showed the following fatty acid composition: $C_{16:0}$—4.0%, $C_{18:0}$—1.0%, $C_{18:1}$—66.5%, $C_{18:2}$—18:4%, $C_{18:3}$—7.2%, saturates—5.0%, Total Saturates—6.1%. In a single location replicated yield trial M3054.7 was not significantly different in yield from the parent cultivar Westar. M3054.7 was crossed to M3052.1 for allelism studies. Fatty acid composition of the $F_2$ seed showed the two lines to be allelic. The mutational events in M3054.7, M3051.10 and M3052.1 although different in origin were in the same gene.

EXAMPLE 6

High Oleic Acid Canola Lines

In the studies of Example 1, at the $M_3$ generation, 31 lines exceeded the upper statistical threshold for oleic acid ($\geq$71.0%). Line W7608.3 had 71.2% oleic acid. At the $M_4$ generation, its selfed progeny (W7608.3.5, since designated A129.5) continued to exceed the upper statistical threshold for $C_{18:1}$ with 78.8% oleic acid. $M_5$ seed of five self-pollinated plants of line A129.5 (ATCC 40811) averaged 75.0% oleic acid. A single plant selection, A129.5.3 had 75.6% oleic acid. The fatty acid composition of this high oleic acid mutant, which was stable under both field and greenhouse conditions to the $M_7$ generation, is summarized in Table IX. This line also stably maintained its mutant fatty acid composition to the $M_7$ generation in field trials in multiple locations. Over all locations the self-pollinated plants (A129) averaged 78.3% oleic acid. The fatty acid composition of the A129 for each Idaho trial location are summarized in Table X. In multiple location replicated yield trials, A129 was not significantly different in yield from the parent cultivar Westar.

The canola oil of A129, after commercial processing, was found to have superior oxidative stability compared to Westar when measured by the Accelerated Oxygen Method (AOM), American Oil Chemists' Society Official Method Cd 12-57 for fat stability; Active Oxygen Method (revised 1989). The AOM of Westar was 18 AOM hours and for A129 was 30 AOM hours.

TABLE IX

Fatty Acid Composition of a High
Oleic Acid Canola Line Produced by Seed Mutagenesis

| | Percent Fatty Acids | | | | | |
|---|---|---|---|---|---|---|
| Genotype | $C_{16:0}$ | $C_{18:0}$ | $C_{18:1}$ | $C_{18:2}$ | $C_{18:3}$ | Sats |
| Westar | 3.9 | 1.9 | 67.5 | 17.6 | 7.4 | 7.0 |
| W7608.3 ($M_3$) | 3.9 | 2.4 | 71.2 | 12.7 | 6.1 | 7.6 |
| W7608.3.5 ($M_4$) | 3.9 | 2.0 | 78.8 | 7.7 | 3.9 | 7.3 |
| A129.5.3 ($M_5$) | 3.8 | 2.3 | 75.6 | 9.5 | 4.9 | 7.6 |

Sats = Total Saturate Content

TABLE X

Fatty Acid Composition of a Mutant High
Oleic Acid Line at Different Field Locations in Idaho

| | Percent Fatty Acids | | | | | |
|---|---|---|---|---|---|---|
| Location | $C_{16:0}$ | $C_{18:0}$ | $C_{18:1}$ | $C_{18:2}$ | $C_{18:3}$ | Sats |
| Burley | 3.3 | 2.1 | 77.5 | 8.1 | 6.0 | 6.5 |
| Tetonia | 3.5 | 3.4 | 77.8 | 6.5 | 4.7 | 8.5 |
| Lamont | 3.4 | 1.9 | 77.8 | 7.4 | 6.5 | 6.3 |
| Shelley | 3.3 | 2.6 | 80.0 | 5.7 | 4.5 | 7.7 |

Sats = Total Saturate Content

The genetic relationship of the high oleic acid mutation A129 to other oleic desaturases was demonstrated in crosses made to commercial canola cultivars and a low linolenic acid mutation. A129 was crossed to the commercial cultivar Global ($C_{16:0}$—4.5%, $C_{18:0}$—1.5%, $C_{18:1}$—62.9%, $C_{18:2}$—20.0%, $C_{18:3}$—7.3%). Approximately 200 $F_2$ individuals were analyzed for fatty acid composition. The results are summarized in Table XB. The segregation fit 1:2:1 ratio suggesting a single co-dominant gene controlled the inheritance of the high oleic acid phenotype.

TABLE XB

Genetic Studies of A129 x Global

| | $C_{18:0}$ | Frequency | |
|---|---|---|---|
| Genotype | Content(%) | Observed | Expected |
| od − od − | 77.3 | 43 | 47 |
| od − od + | 71.7 | 106 | 94 |
| od + od + | 66.1 | 49 | 47 |

A cross between A129 and IMC 01, a low linolenic acid variety ($C_{16:0}$—4.1%, $C_{18:0}$—1.9%, $C_{18:1}$—66.4%, $C_{18:2}$—18.1%, $C_{18:3}$—5.7%), was made to determine the inheritance of the oleic acid desaturase and linoleic acid desaturase. In the $F_1$ hybrids both the oleic acid and linoleic acid desaturase genes approached the mid-parent values indicating a co-dominant gene actions. Fatty acid analysis of the $F_2$ individuals confirmed a 1:2:1:2:4:2:1:2:1 segregation of two independent, co-dominant genes (Table XC). A line was selected from the cross of A129 and IMC01 and designated as IMC130 (ATCC deposit no. 75446) as described in U.S. patent application Ser. No. 08/425,108, incorporated herein by reference.

TABLE XC

Genetic Studies of A129 x IMC 01

| | | Frequency | |
|---|---|---|---|
| Genotype | Ratio | Observed | Expected |
| od − od − ld − ld − | 1 | 11 | 12 |
| od − od − ld − ld + | 2 | 30 | 24 |
| od − od − ld + ld + | 1 | 10 | 12 |
| od − od + ld − ld − | 2 | 25 | 24 |
| od − od + ld − ld + | 4 | 54 | 47 |
| od − od + ld + ld + | 2 | 18 | 24 |
| od + od + ld − ld − | 1 | 7 | 12 |
| od + od + ld − ld + | 2 | 25 | 24 |
| od + od + ld + ld + | 1 | 8 | 12 |

An additional high oleic acid line, designated A128.3, was also produced by the disclosed method. A 50-seed bulk analysis of this line showed the following fatty acid composition: $C_{16:0}$—3.5%, $C_{18:0}$—1.8%, $C_{18:1}$—77.3%, $C_{18:2}$—9.0%, $C_{18:3}$—5.6%, FDA Sats—5.3%, Total Sats—6.4%. This line also stably maintained its mutant fatty acid composition to the $M_7$ generation. In multiple locations replicated yield trials, A128 was not significantly different in yield from the parent cultivar Westar.

A129 was crossed to A128.3 for allelism studies. Fatty acid composition of the $F_2$ seed showed the two lines to be allelic. The mutational events in A129 and A128.3 although different in origin were in the same gene.

An additional high oleic acid line, designated M3028.-10 (ATCC 75026), was also produced by the disclosed method in Example 1. A 10-seed bulk analysis of this line showed the following fatty acid composition: $C_{16:0}$—3.5%, $C_{18:0}$—1.8%, $C_{18:1}$—77.3%, $C_{18:2}$—9.0%, $C_{18:3}$—5.6%, FDA Saturates—5.3%, Total Saturates—6.4%. In a single location replicated yield trial M3028.10 was not significantly different in yield from the parent cultivar Westar.

EXAMPLE 7

Low Linoleic Acid Canola

In the studies of Example 1, at the $M_3$ generation, 80 lines exceeded the lower statistical threshold for linoleic acid (<13.2%). Line W12638.8 had 9.4% linoleic acid. At the $M_4$ and $M_5$ generations, its selfed progenies [W12638.8, since designated A 133.1 (ATCC 40812)] continued to exceed the statistical threshold for low $C_{1-8:2}$ with linoleic acid levels of 10.2% and 8.4%, respectively. The fatty acid composition of this low linoleic acid mutant, which was stable to the $M_7$ generation under both field and greenhouse conditions, is summarized in Table XI. In multiple location replicated yield trials, A133 was not significantly different in yield from the parent cultivar Westar. An additional low linoleic acid line, designated M3062.8 (ATCC 75025), was also produced by the disclosed method. A 10-seed bulk analysis of this line showed the following fatty acid composition: $C_{16:0}$—3.8%, $C_{18:0}$—2.3%, $C_{18:1}$—77.1%, $C_{18:2}$—8.9%, $C_{18:3}$—4.3%, FDA Sats—6.1%. This line has also stably maintained its mutant fatty acid composition in the field and greenhouse.

TABLE XI

Fatty Acid Composition of a Low
Linoleic Acid Canola Line Produced by Seed Mutagenesis

| Genotype[a] | Percent Fatty Acids | | | | | |
|---|---|---|---|---|---|---|
| | $C_{16:0}$ | $C_{18:0}$ | $C_{18:1}$ | $C_{18:2}$ | $C_{18:3}$ | Sats[b] |
| Westar | 3.9 | 1.9 | 67.5 | 17.6 | 7.4 | 7.0 |
| W12638.8 ($M_3$) | 3.9 | 2.3 | 75.0 | 9.4 | 6.1 | 7.5 |
| W12638.8.1 ($M_4$) | 4.1 | 1.7 | 74.6 | 10.2 | 5.9 | 7.1 |
| A133.1.8 ($M_5$) | 3.8 | 2.0 | 77.7 | 8.4 | 5.0 | 7.0 |

[a]Letter and numbers up to second decimal point indicate the plant line.
Number after second decimal point indicates an individual plant.
[b]Sats = Total Saturate Content

EXAMPLE 8

Low Linolenic and Linoleic Acid Canola

In the studies of Example 1, at the $M_3$ generation, 57 lines exceeded the lower statistical threshold for linolenic acid (≦5.3%). Line W14749.8 had 5.3% linolenic acid and 15.0% linoleic acid. At the $M_4$ and $M_5$ generations, its selfed progenies [W14749.8, since designated M3032 (ATCC 75021)] continued to exceed the statistical threshold for low $C_{18:3}$ with linolenic acid levels of 2.7% and 2.3%, respectively, and for a low sum of linolenic and linoleic acids with totals of 11.8% and 12.5% respectively. The fatty acid composition of this low linolenic acid plus linoleic acid mutant, which was stable to the $M_5$ generation under both field and greenhouse conditions, is summarized in Table XII. In a single location replicated yield trial M3032 was not significantly different in yield from the parent cultivar (Westar).

TABLE XII

Fatty Acid Composition of a Low
Linolenic Acid Canola Line Produced by Seed Mutagenesis

| Genotype | Percent Fatty Acids | | | | | |
|---|---|---|---|---|---|---|
| | $C_{16:0}$ | $C_{18:0}$ | $C_{18:1}$ | $C_{18:2}$ | $C_{18:3}$ | Sats |
| Westar | 3.9 | 1.9 | 67.5 | 17.6 | 7.4 | 7.0 |
| W14749.8 ($M_3$) | 4.0 | 2.5 | 69.4 | 15.0 | 5.3 | 6.5 |
| M3032.8 ($M_4$) | 3.9 | 2.4 | 77.9 | 9.1 | 2.7 | 6.4 |
| M3032.1 ($M_5$) | 3.5 | 2.8 | 80.0 | 10.2 | 2.3 | 6.5 |

Sats = Total Saturate Content

EXAMPLE 9

The high oleic acid mutation of A129 was introduced into different genetic backgrounds by crossing and selecting for fatty acid and agronomic characteristics. A1129 (now renamed IMC 129) was crossed to Legend, a commercial spring Brassica napus variety. Legend has the following fatty acid composition: $C_{16:0}$—3.8%, $C_{18:0}$—2.1%, $C_{18:1}$—63.1%, $C_{18:2}$—17.8%, $C_{18:3}$—9.3%. The cross and progeny resulting from were coded as 89B60303.

The $F_1$ seed resulting from the cross was planted in the greenhouse and self-pollinated to produce $F_2$ seed. The $F_2$ seed was planted in the field for evaluation. Individual plants were selected in the field for agronomic characteristics. At maturity, the $F_3$ seed was harvested from each selected plant and analyzed for fatty acid composition.

Individuals which had fatty acid profiles similar to the high oleic acid parent (IMC 129) were advanced back to the field. Seeds ($F_3$) of selected individuals were planted in the field as selfing rows and in plots for preliminary yield and agronomic evaluations. At flowering the $F_3$ plants in the selfing rows were self-pollinated. At maturity the $F_4$ seed was harvested from individual plants to determine fatty acid composition. Yield of the individual selections was determined from the harvested plots.

Based on fatty acid composition of the individual plants and yield and agronomic characteristics of the plots $F_4$ lines were selected and advanced to the next generation in the greenhouse. Five plants from each selected line were self-pollinated. At maturity the $F_5$ seed was harvested from each and analyzed for fatty acid composition.

The $F_5$ line with the highest oleic fatty profile was advanced to the field as a selfing row. The remaining $F_5$ seed from the five plants was bulked together for planting the yield plots in the field. At flowering, the $F_5$ plants in each selfing-row were self-pollinated. At maturity the $F_6$ self-pollinated seed was harvest from the selfing row to determine fatty acid composition and select for the high oleic acid trait. Yield of the individual selections was determined from the harvested plots.

Fifteen $F_6$ lines having the high oleic fatty profile of IMC 129 and the desired agronomic characteristics were advanced to the greenhouse to increase seed for field trialing. At flowering the $F_6$ plants were self-pollinated. At maturity the $F_7$ seed was harvested and analyzed for fatty acid composition. Three $F_7$ seed lines which had fatty acid profiles most similar to IMC 129 (Table XIII) were selected and planted in the field as selfing rows, the remaining seed was bulked together for yield trialing. The high oleic fatty acid profile of IMC 129 was maintained through seven generations of selection for fatty acid and agronomic traits in an agronomic background of Brassica napus which was different from the parental lines. Thus, the genetic trait from IMC 129 for high oleic acid can be used in the development of new high oleic Brassica napus varieties.

TABLE XIII

Fatty Acid Composition of Advanced Breeding Generation
with High Oleic Acid Trait (IMC 129 X Legend)

| $F_7$ Selections of 89B60303 | Fatty Acid Composition (%) | | | | |
|---|---|---|---|---|---|
| | $C_{16:0}$ | $C_{18:0}$ | $C_{18:1}$ | $C_{18:2}$ | $C_{18:3}$ |
| 93.06194 | 3.8 | 1.6 | 78.3 | 7.7 | 4.4 |
| 93.06196 | 4.0 | 2.8 | 77.3 | 6.8 | 3.4 |
| 93.06198 | 3.7 | 2.2 | 78.0 | 7.4 | 4.2 |

The high oleic acid trait of IMC 129 was also introduced into a different genetic background by combining crossing and selection methods with the generation of dihaploid populations from the microspores of the $F_1$ hybrids. IMC 129 was crossed to Hyola 41, a commercial spring Brassica napus variety. Hyola 41 has the following fatty acid composition: $C_{16:0}$—3.8%, $C_{18:0}$—2.7%, $C_{18:1}$—64.9%, $C_{18:2}$—16.2%, $C_{18:3}$—9.1%. The cross and progeny resulting from the cross were labeled 90DU. 146.

The $F_1$ seed was planted from the cross and a dihaploid ($DH_1$) population was made from the $F_1$ microspores using standard procedures for *Brassica napus*. Each $DH_1$ plant was self-pollinated at flowering to produce $DH_1$ seed. At maturity the $DH_1$ seed was harvested and analyzed for fatty acid composition. $DH_1$ individuals which expressed the high oleic fatty acid profit of IMC 129 were advanced to the next generation in the greenhouse. For each individual selected five $DH_1$ seeds were planted. At flowering the $DH_2$ plants were self-pollinated. At maturity the $DH_2$ seed was harvested and analyzed for fatty acid composition. The $DH_2$ seed which was similar in fatty acid composition to the IMC 129 parent was advanced to the field as a selfing row. The remaining $DH_2$ seed of that group was bulked and planted in plots to determine yield and agronomic characteristics of the line. At flowering individual $DH_3$ plants in the selfing row were self-pollinated. At maturity the $DH_3$ seed was harvested from the individual plants to determine fatty acid composition. Yield of the selections was determined from the harvested plots. Based on fatty acid composition, yield and agronomic characteristics selections were advanced to the next generation in the greenhouse. The $DH_4$ seed produced in the greenhouse by self-pollination was analyzed for fatty acid composition. Individuals which were similar to the fatty acid composition of the IMC 129 parent were advanced to the field to test for fatty acid stability and yield evaluation. The harvested $DH_5$ seed from six locations maintained the fatty acid profile of the IMC 129 parent (Table XIV).

TABLE XIV

Fatty Acid Composition of Advanced Dihaploid Breeding Generation with High Oleic Acid Trait (IMC 129 X Hyola 41)

| DH5 of 90DU.146 at Multiple Locations | Fatty Acid Composition (%) | | | | |
|---|---|---|---|---|---|
| | $C_{16:0}$ | $C_{18:0}$ | $C_{18:1}$ | $C_{18:2}$ | $C_{18:3}$ |
| Aberdeen | 3.7 | 2.6 | 75.4 | 8.1 | 7.2 |
| Blackfoot | 3.3 | 2.4 | 75.5 | 8.8 | 7.5 |
| Idaho Falls | 3.7 | 3.1 | 75.0 | 7.5 | 8.1 |
| Rexberg | 3.9 | 3.7 | 75.3 | 7.0 | 6.5 |
| Swan Valley | 3.5 | 3.4 | 74.5 | 7.0 | 7.3 |
| Lamont | 3.9 | 2.8 | 72.0 | 10.1 | 8.4 |

EXAMPLE 10

Canola Line 0508

Seeds of the *B. napus* line IMC-129 were mutagenized with methyl N-nitrosoguanidine (MNNG). The MNNG treatment consisted of three parts: pre-soak, mutagen application, and wash. A 0.05M Sorenson's phosphate buffer was used to maintain pre-soak and mutagen treatment pH at 6.1. Two hundred seeds were treated at one time on filter paper (Whatman #3M) in a petri dish (100 mm×15 mm). The seeds were pre-soaked in 15 mls of 0.05M Sorenson's buffer, pH 6.1, under continued agitation for two hours. At the end of the pre-soak period, the buffer was removed from the plate.

A 10 mM concentration of MNNG in 0.05M Sorenson's buffer, pH 6.1, was prepared prior to use. Fifteen ml of 10 m MNNG was added to the seeds in each plate. The seeds were incubated at 22° C.±3° C. in the dark under constant agitation for four (4) hours. At the end of the incubation period, the mutagen solution was removed.

The seeds were washed with three changes of distilled water at 10 minute intervals. The fourth wash was for thirty minutes. This treatment regime produced an LD60 population.

Treated seeds were planted in standard greenhouse potting soil and placed into an environmentally controlled greenhouse. The plants were grown under sixteen hours of light. At flowering, the racemes were bagged to produce selfed seed. At maturity, the M2 seed was harvested. Each M2 line was given an identifying number. The entire MNNG-treated seed population was designated as the Q series.

Harvested M2 seeds was planted in the greenhouse. The growth conditions were maintained as previously described. The racemes were bagged at flowering for selfing. At maturity, the selfed M3 seed was harvested and analyzed for fatty acid composition. For each M3 seed line, approximately 10-15 seeds were analyzed in bulk as described in Example 1.

High oleic-low linoleic M3 lines were selected from the M3 population using a cutoff of >82% oleic acid and <50% linoleic. From the first 1600 M3 lines screened for fatty acid composition, Q508 was identified. Table XV shows the fatty acid composition of Q508, Westar and IMC 129. The Q508 M3 generation was advanced to the M4 generation in the greenhouse. The M4 selfed seed maintained the selected high oleic-low linoleic acid phenotype (Table XVI).

Nine other M4 high-oleic low-linoleic lines were also identified: Q3603, Q3733, Q4249, Q6284, Q6601, Q6761, Q7415, Q4275, and Q6676. Some of these lines had good agronomic characteristics and an elevated oleic acid level in seeds of about 80% to about 84%.

TABLE XV

Fatty Acid Composition of A129 and High Oleic Acid M3 Mutant 0508

| Line # | 16:0 | 18:0 | 18:1 | 18:2 | 18:3 |
|---|---|---|---|---|---|
| A129* | 4.0 | 2.4 | 77.7 | 7.8 | 4.2 |
| Q508 | 3.9 | 2.1 | 84.9 | 2.4 | 2.9 |

*Fatty acid composition of A129 is the average of 50 self-pollinated plants grown with the M3 population $M_4$ generation Q508 plants had poor agronomic qualities in the field compared to Westar. Typical plants were slow growing relative to Westar, lacked early vegetative vigor, were short in stature, tended to be chlorotic and had short pods. The yield of Q508 was very low compared to Westar.

The $M_4$ generation Q508 plants in the greenhouse tended to be reduced in vigor compared to Westar. However, Q508 yields in the greenhouse were greater than Q508 yields in the field.

TABLE XVI

Fatty Acid Composition of Seed Oil from Greenhouse-Grown Q508, IMC129 and Westar.

| Line | 16:0 | 18:0 | 18:1 | 18:2 | 18:3 | FDA Sats |
|---|---|---|---|---|---|---|
| IMC129[a] | 4.0 | 2.4 | 77.7 | 7.8 | 4.2 | 6.4 |
| Westar[b] | 3.9 | 1.9 | 67.5 | 17.6 | 7.4 | >5.8 |
| Q508[c] | 3.9 | 2.1 | 84.9 | 2.4 | 2.9 | 6.0 |

[a]Average of 50 self-pollinated plants
[b]Data from Example 1
[c]Average of 50 self-pollinated plants $M_4$ generation Q508 plants were crossed to a dihaploid selection of Westar, with Westar serving as the female parent. The resulting F1 seed was termed the 92EF population. About 126 µl individuals that appeared to have better agronomic characteristics than the Q508 parent were selected for selfing. A portion of the $F_2$ seed from such individuals was replanted in the field. Each F2 plant was selfed and a portion of the resulting F3 seed was analyzed for fatty acid composition. The content of oleic acid in $F_3$ seed ranged from 59 to 79%. No high oleic (>80%) individuals were recovered with good agronomic type.

TABLE XVII

| LOCATION | SITE CHARACTERISTICS |
|---|---|
| BURLEY | Irrigated. Long season. High temperatures during flowering. |
| TETONIA | Dryland. Short season. Cool temperatures. |
| LAMONT | Dryland. Short season. Cool temperatures. |
| SHELLEY | Irrigated. Medium season. High temperatures during flowering. |

Yield of the entries in the trial was determined by taking the statistical average of the four replications. The Least Significant Difference Test was used to rank the entries in the randomized complete block design.

A portion of the $F_2$ seed of the 92EF population was planted in the greenhouse to analyze the genetics of the Q508 line. $F_3$ seed was analyzed from 380 F2 individuals. The $C_{18:1}$ levels of $F_3$ seed from the greenhouse experiment is depicted in FIG. 3. The data were tested against the hypothesis that Q508 contains two mutant genes that are semi-dominant and additive: the original IMC129 mutation as well as one additional mutation. The hypothesis also assumes that homozygous Q508 has greater than 85% oleic acid and homozygous Westar has 62-67% oleic acid. The possible genotypes at each gene in a cross of Q508 by Westar may be designated as:

AA=Westar Fad2$^a$
BB=Westar Fad2$^b$
aa=Q508 Fad2$^{a-}$
bb=Q508 Fad2$^{b-}$

Assuming independent segregation, a 1:4:6:4:1 ratio of phenotypes is expected. The phenotypes of heterozygous plants are assumed to be indistinguishable and, thus, the data were tested for fit to a 1:14:1 ratio of homozygous Westar: heterozygous plants: homozygous Q508.

| Phenotypic Ratio | # of Westar Alleles | Genotype |
|---|---|---|
| 1 | 4 | AABB(Westar) |
| 4 | 3 | AABb,AaBB,AABb,AaBB |
| 6 | 2 | AaBb,AAbb,AaBb,AaBb,aaBB,AaBB |
| 4 | 1 | Aabb,aaBb,Aabb,aaBb |
| 1 | 0 | aabb (Q508) |

Using Chi-square analysis, the oleic acid data fit a 1:14:1 ratio. It was concluded that Q508 differs from Westar by two major genes that are semi-dominant and additive and that segregate independently. By comparison, the genotype of IMC129 is aaBB.

The fatty acid composition of representative F3 individuals having greater than 85% oleic acid in seed oil is shown in Table XVIII. The levels of saturated fatty acids are seen to be decreased in such plants, compared to Westar.

TABLE XVIII

| 92EF $F_3$ Individuals with >85% $C_{18:1}$ in Seed Oil | | | | | | |
|---|---|---|---|---|---|---|
| F3 Plant | Fatty Acid Compostion (%) | | | | | |
| Identifier | C16:0 | C18:0 | C18:1 | C18:2 | C18:3 | FDASA |
| +38068 | 3.401 | 1.582 | 85.452 | 2.134 | 3.615 | 4.983 |
| +38156 | 3.388 | 1.379 | 85.434 | 2.143 | 3.701 | 4.767 |
| +38171 | 3.588 | 1.511 | 85.289 | 2.367 | 3.425 | 5.099 |
| +38181 | 3.75 | 1.16 | 85.312 | 2.968 | 3.819 | 4.977 |
| +38182 | 3.529 | 0.985 | 85.905 | 2.614 | 3.926 | 4.56 |
| +38191 | 3.364 | 1.039 | 85.737 | 2.869 | 4.039 | 4.459 |
| +38196 | 3.557 | 1.182 | 85.054 | 2.962 | 4.252 | 4.739 |
| +38202 | 3.554 | 1.105 | 86.091 | 2.651 | 3.721 | 4.713 |
| +38220 | 3.093 | 1.16 | 86.421 | 1.931 | 3.514 | 4.314 |
| +38236 | 3.308 | 1.349 | 85.425 | 2.37 | 3.605 | 4.718 |
| +38408 | 3.617 | 1.607 | 85.34 | 2.33 | 3.562 | 5.224 |
| +38427 | 3.494 | 1.454 | 85.924 | 2.206 | 3.289 | 4.948 |
| +38533 | 3.64 | 1.319 | 85.962 | 2.715 | 3.516 | 4.959 |

EXAMPLE 11

Leaf and Root Fatty Acid Profiles of Canola Lines IMC-129, Q508, and Westar

Plants of Q508, IMC 129 and Westar were grown in the greenhouse. Mature leaves, primary expanding leaves, petioles and roots were harvested at the 6-8 leaf stage, frozen in liquid nitrogen and stored at −70° C. Leaf lipid extracts were analyzed by GLC as described in Example 1. The fatty acid profile data are shown in Table XIX.

The data in Table XIX indicate that total leaf lipids in Q508 are higher in $C_{18:1}$ content than the $C_{18:2}$ plus $C_{18:3}$ content. The reverse is true for Westar and IMC 129. The difference in total leaf lipids between Q508 and IMC 129 is consistent with the hypothesis that a second Fad2 gene is mutated in Q508.

The $C_{16:3}$ content in the total lipid fraction was about the same for all three lines, suggesting that the plastid FadC gene product was not affected by the Q508 mutations. To confirm that the FadC gene was not mutated, chloroplast lipids were separated and analyzed. No changes in chloroplast $C_{16:1}$, $C_{16:2}$ or $C_{16:3}$ fatty acids were detected in the three lines. The similarity in plastid leaf lipids among Q508, Westar and IMC129 is consistent with the hypothesis that the second mutation in Q508 affects a microsomal Fad2 gene and not a plastid FadC gene.

TABLE XIX

| | MATURE LEAF | | | EXPANDING LEAF | | | PETIOLE | | | ROOT | | |
|---|---|---|---|---|---|---|---|---|---|---|---|---|
| | West. | 129 | 3Q508 | West. | 129 | 3Q508 | West. | 129 | 3Q508 | West. | 129 | 3Q508 |
| 16:0 | 12.1 | 11.9 | 10.1 | 16.4 | 16.1 | 11.3 | 21.7 | 23.5 | 11.9 | 21.1 | 21.9 | 12.0 |
| 16:1 | 0.8 | 0.6 | 1.1 | 0.7 | 0.6 | 1.1 | 1.0 | 1.3 | 1.4 | | | |
| 16:2 | 2.3 | 2.2 | 2.0 | 2.8 | 3.1 | 2.8 | 1.8 | 2.2 | 1.8 | | | |
| 16:3 | 14.7 | 15.0 | 14.0 | 6.3 | 5.4 | 6.9 | 5.7 | 4.6 | 5.7 | | | |
| 18:0 | 2.2 | 1.6 | 1.2 | 2.5 | 2.8 | 1.5 | 3.7 | 4.0 | 1.6 | 3.6 | 2.9 | 2.5 |
| 18:1 | 2.8 | 4.9 | 16.7 | 3.8 | 8.3 | 38.0 | 4.9 | 12.9 | 46.9 | 3.5 | 6.1 | 68.8 |
| 18:2 | 12.6 | 11.5 | 6.8 | 13.3 | 13.8 | 4.9 | 20.7 | 18.3 | 5.2 | 28.0 | 30.4 | 4.4 |
| 18:3 | 50.6 | 50.3 | 46.0 | 54.2 | 50.0 | 33.5 | 40.4 | 33.2 | 25.3 | 43.8 | 38.7 | 12.3 |

EXAMPLE 12

Sequences of Mutant and Wild-Type Delta-12 Fatty Acid Desaturases from *B. napus*

Primers specific for the FAD2 structural gene were used to clone the entire open reading frame (ORF) of the D and F 12-DES genes by reverse transcriptase polymerase chain reaction (RT-PCR). RNA from seeds of IMC129, Q508 and Westar plants was isolated by standard methods and was used as template. The RT-amplified fragments were used for nucleotide sequence determination. The DNA sequence of each gene from each line was determined from both strands by standard dideoxy sequencing methods.

Sequence analysis revealed a G to A transversion at nucleotide 316 (from the translation initiation codon) of the D gene in both IMC 129 and Q508, compared to the sequence of Westar. The transversion changes the codon at this position from GAG to AAG and results in a non-conservative substitution of glutamic acid, an acidic residue, for lysine a basic residue. The presence of the same mutation in both lines was expected since the Q508 line was derived from IMC129. The same base change was also detected in Q508 and IMC 129 when RNA from leaf tissue was used as template.

The G to A mutation at nucleotide 316 was confirmed by sequencing several independent clones containing fragments amplified directly from genomic DNA of IMC129 and Westar. These results eliminated the possibility of a rare mutation introduced during reverse transcription and PCR in the RT-PCR protocol. It was concluded that the IMC129 mutant is due to a single base transversion at nucleotide 316 in the coding region of the D gene of rapeseed microsomal delta 12-desaturase.

A single base transition from T to A at nucleotide 515 of the F gene was detected in Q508 compared to the Westar sequence. The mutation changes the codon at this position from CTC to CAC, resulting in the non-conservative substitution of a non-polar residue, leucine, for a polar residue, histidine, in the resulting gene product. No mutations were found in the F gene sequence of IMC129 compared to the F gene sequence of Westar.

These data support the conclusion that a mutation in a delta-12 desaturase gene sequence results in alterations in the fatty acid profile of plants containing such a mutated gene. Moreover, the data show that when a plant line or species contains two delta-12 desaturase loci, the fatty acid profile of an individual having two mutated loci differs from the fatty acid profile of an individual having one mutated locus.

The mutation in the D gene of IMC129 and Q508 mapped to a region having a conserved amino acid motif (His-Xaa-Xaa-Xaa-His) found in cloned delta-12 and delta-15 membrane bound-desaturases (Table XX).

TABLE XX

Alignment of Amino Acid Sequences of Cloned Canola Membrane Bound-Desaturases

| Desaturase Gene | Sequence[a] | Position[b] |
|---|---|---|
| Canola-fad2-D(129) | AHKCGH (SEQ ID NO:40) | 109 |
| Canola-FAd2-D | AHECGH (SEQ ID NO:41) | 109 |
| Canola-FAd2-F | AHECGH (SEQ ID NO:41) | 109 |
| Canola FadC | GH<u>DCA</u>H (SEQ ID NO:42) | 170 |
| Canola-Fad3 | GH<u>DC</u>GH (SEQ ID NO:43) | 96 |
| Canola-FadD | GH<u>DC</u>GH (SEQ ID NO:43) | 125 |

(FadD = Plastid delta 15, Fad3 = Microsomal delta-15),
(FadC = Plastid delta-12, Fad2 = Microsomal delta-12)
[a]One letter amino acid code; conservative substitutions are underlined; non-conservative substitutions are in bold.
[b]position of first amino acid in gene product.

EXAMPLE 13

Transcription and Translation of Microsomal Delta-12 Fatty Acid Desaturases

Transcription in vivo was analyzed by RT-PCR analysis of stage II and stage III developing seeds and leaf tissue. The primers used to specifically amplify 12-DES F gene RNA from the indicated tissues were sense primer 5'-GGATAT-GATGATGGTGAAAGA-3' (SEQ ID NO:44) and antisense primer 5'-TCTTTCACCATCATCATATCC-3' (SEQ ID NO:45). The primers used to specifically amplify 12-DES D gene RNA from the indicated tissues were sense primer 5'-GTTATGAAGCAAAGAAGAAAC-3' (SEQ ID NO:46) and antisense primer 5'-GTTTCTTCTTTGCTTCATAAC-3' (SEQ ID NO:47). The results indicated that mRNA of both the D and F gene was expressed in seed and leaf tissues of IMC129, Q508 and wild type Westar plants.

In vitro transcription and translation analysis showed that a peptide of about 46 kD was made. This is the expected size of both the D gene product and the F gene product, based on sum of the deduced amino acid sequence of each gene and the cotranslational addition of a microsomal membrane peptide.

These results rule out the possibility that non-sense or frameshift mutations, resulting in a truncated polypeptide gene product, are present in either the mutant D gene or the mutant F gene. The data, in conjunction with the data of Example 12, support the conclusion that the mutations in Q508 and IMC129 are in delta-12 fatty acid desaturase structural genes encoding desaturase enzymes, rather than in regulatory genes.

EXAMPLE 14

Development of Gene-Specific PCR Markers

Based on the single base change in the mutant D gene of IMC129 described in above, two 5' PCR primers were designed. The nucleotide sequence of the primers differed only in the base (G for Westar and A for IMC129) at the 3' end. The primers allow one to distinguish between mutant Can-Fad2-D-129 and wild-type Can-Fad2-D alleles in a DNA-based PCR assay. Since there is only a single base difference in the 5' PCR primers, the PCR assay is very sensitive to the PCR conditions such as annealing temperature, cycle number, amount, and purity of DNA templates used. Assay conditions have been established that distinguish between the mutant gene and the wild type gene using genomic DNA from IMC 129 and wild type plants as templates. Conditions may be further optimized by varying PCR parameters, particularly with variable crude DNA samples. A PCR assay distinguishing the single base mutation in IMC 129 from the wild type gene along with fatty acid composition analysis provides a means to simplify segregation and selection analysis of genetic crosses involving plants having a delta-12 fatty acid desaturase mutation.

To the extent not already indicated, it will be understood by those of ordinary skill in the art that any one of the various specific embodiments herein described and illustrated may be further modified to incorporate features shown in other of the specific embodiments.

The foregoing detailed description has been provided for a better understanding of the invention only and no unnecessary limitation should be understood therefrom as some modifications will be apparent to those skilled in the art without deviating from the spirit and scope of the appended claims.

What is claimed is:

1. A Brassicaceae plant containing a full-length coding sequence of a delta-12 fatty acid desaturase gene, the gene product encoded by said sequence having at least one mutation in a His-Glu-Cys-Gly-His (SEQ ID NO:9) amino acid motif, and wherein said mutation renders said gene product non-functional and confers an altered fatty acid composition in seeds of said plant.

2. The plant of claim 1, wherein said mutation confers a decreased linoleic acid level in said seeds.

3. The plant of claim 1, wherein said at least one mutation comprises a non-conservative amino acid substitution in said motif.

4. The plant of claim 1, wherein said gene is a *Brassica napus* gene.

5. The plant of claim 1, wherein said plant is a *Brassica napus* plant.

6. The plant of claim 3, wherein said at least one mutation in said motif comprises a codon encoding Lys in place of the codon encoding Glu.

7. A *Brassica* plant containing a full-length coding sequence of a delta-12 fatty acid desaturase gene, the gene product encoded by said sequence comprising at least one mutation in a His-Glu-Cys-Gly-His (SEQ ID NO:9) amino acid motif, and wherein said mutation renders said gene product non-functional and confers an altered fatty acid composition in seeds of said plant.

8. The *Brassica* plant of claim 7, wherein said at least one mutation in said motif comprises a codon encoding Lys in place of the codon encoding Glu.

9. A *Brassica* plant containing a full-length coding sequence of a delta-12 fatty acid desaturase gene, the gene product encoded by said sequence comprising a non-conservative amino acid substitution in a His-Glu-Cys-Gly-His (SEQ ID NO:9) amino acid motif, and wherein said mutation renders said gene product non-functional and confers an altered fatty acid composition in seeds of said plant.

10. The *Brassica* plant of claim 9, wherein said at least one mutation in said motif comprises a codon encoding Lys in place of the codon encoding Glu.

11. The *Brassica* plant of claim 9, wherein said plant is a *Brassica napus*, *Brassica rapa*, or *Brassica juncea* plant.

12. The *Brassica* plant of claim 11, wherein said plant is a *Brassica napus* plant.

13. A *Brassica* plant containing a full-length coding sequence of a *Brassica* delta-12 fatty acid desaturase gene, the gene product encoded by said sequence comprising at least one mutation in a His-Glu-Cys-Gly-His (SEQ ID NO:9) amino acid motif, and wherein said mutation renders said gene product non-functional and confers an altered fatty acid composition in seeds of said plant.

14. A *Brassica napus* plant containing a mutation in an endogenous delta-12 fatty acid desaturase, said mutation comprising substitution of a Lys for Glu in a His-Glu-Cys-Gly-His (SEQ ID NO:9) amino acid motif, and wherein said mutation confers an increase in oleic acid content in seeds of said plant relative to that of seeds of a *Brassica napus* plant lacking said mutation in said endogenous delta-12 fatty acid desaturase gene.

15. The plant of claim 14, wherein seeds of said plant containing said mutation have an oleic acid content of 71% to 78%.

16. Previously presented) Progeny of said *Brassica napus* plant of claim 14, said progeny comprising said mutation in said endogenous delta-12 fatty acid desaturase gene.

* * * * *

UNITED STATES PATENT AND TRADEMARK OFFICE
CERTIFICATE OF CORRECTION

PATENT NO. : 7,262,343 B1 Page 1 of 1
APPLICATION NO. : 09/064277
DATED : August 28, 2007
INVENTOR(S) : Lorin R. DeBonte, Guo-Hua Miao and Zhegong Fan It is certified that error appears in the above-identified patent and that said Letters Patent is hereby corrected as shown below:

Title Page, please insert under (*) Notice: --This patent is subject to a terminal disclaimer--;

Column 68, line 30, please delete "Previously presented)".

Signed and Sealed this

Sixteenth Day of September, 2008

JON W. DUDAS
*Director of the United States Patent and Trademark Office*

SEQUENCE LISTING

```
<160> NUMBER OF SEQ ID NOS: 49

<210> SEQ ID NO 1
<211> LENGTH: 1155
<212> TYPE: DNA
<213> ORGANISM: Brassica napus
<220> FEATURE:
<221> NAME/KEY: CDS
<222> LOCATION: (1)...(1152)
<223> OTHER INFORMATION: wild type D form
<220> FEATURE:
<221> NAME/KEY: misc_feature
<222> LOCATION: 205
<223> OTHER INFORMATION: n = A,T,C or G

<400> SEQUENCE: 1 atg ggt gca ggt gga aga atg caa gtg tct cct ccc tcc aag aag tct      48
Met Gly Ala Gly Gly Arg Met Gln Val Ser Pro Pro Ser Lys Lys Ser
 1               5                  10                  15 gaa acc gac acc atc aag cgc gta ccc tgc gag aca ccg ccc ttc act      96
Glu Thr Asp Thr Ile Lys Arg Val Pro Cys Glu Thr Pro Pro Phe Thr
                 20                  25                  30 gtc gga gaa ctc aag aaa gca atc cca ccg cac tgt ttc aaa cgc tcg     144
Val Gly Glu Leu Lys Lys Ala Ile Pro Pro His Cys Phe Lys Arg Ser
             35                  40                  45 atc cct cgc tct ttc tcc tac ctc atc tgg gac atc atc ata gcc tcc     192
Ile Pro Arg Ser Phe Ser Tyr Leu Ile Trp Asp Ile Ile Ile Ala Ser
         50                  55                  60 tgc ttc tac tac ntc gcc acc act tac ttc cct ctc ctc cct cac cct     240
Cys Phe Tyr Tyr Xaa Ala Thr Thr Tyr Phe Pro Leu Leu Pro His Pro
 65                  70                  75                  80 ctc tcc tac ttc gcc tgg cct ctc tac tgg gcc tgc caa ggg tgc gtc     288
Leu Ser Tyr Phe Ala Trp Pro Leu Tyr Trp Ala Cys Gln Gly Cys Val
                 85                  90                  95 cta acc ggc gtc tgg gtc ata gcc cac gaa tgc ggc cac cac gcc ttc     336
Leu Thr Gly Val Trp Val Ile Ala His Glu Cys Gly His His Ala Phe
                100                 105                 110 agc gac tac cag tgg ctt gac gac acc gtc ggt ctc atc ttc cac tcc     384
Ser Asp Tyr Gln Trp Leu Asp Asp Thr Val Gly Leu Ile Phe His Ser
            115                 120                 125 ttc ctc ctc gtc cct tac ttc tcc tgg aag tac agt cat cgc agc cac     432
```

```
                Phe Leu Leu Val Pro Tyr Phe Ser Trp Lys Tyr Ser His Arg Ser His
                    130                 135                 140 cat tcc aac act ggc tcc ctc gag aga gac gaa gtg ttt gtc ccc aag         480
His Ser Asn Thr Gly Ser Leu Glu Arg Asp Glu Val Phe Val Pro Lys
145                 150                 155                 160 aag aag tca gac atc aag tgg tac ggc aag tac ctc aac aac cct ttg         528
Lys Lys Ser Asp Ile Lys Trp Tyr Gly Lys Tyr Leu Asn Asn Pro Leu
                165                 170                 175 gga cgc acc gtg atg tta acg gtt cag ttc act ctc ggc tgg ccg ttg         576
Gly Arg Thr Val Met Leu Thr Val Gln Phe Thr Leu Gly Trp Pro Leu
            180                 185                 190 tac tta gcc ttc aac gtc tcg gga aga cct tac gac ggc ggc ttc cgt         624
Tyr Leu Ala Phe Asn Val Ser Gly Arg Pro Tyr Asp Gly Gly Phe Arg
        195                 200                 205 tgc cat ttc cac ccc aac gct ccc atc tac aac gac cgc gag cgt ctc         672
Cys His Phe His Pro Asn Ala Pro Ile Tyr Asn Asp Arg Glu Arg Leu
    210                 215                 220 cag ata tac atc tcc gac gct ggc atc ctc gcc gtc tgc tac ggt ctc         720
Gln Ile Tyr Ile Ser Asp Ala Gly Ile Leu Ala Val Cys Tyr Gly Leu
225                 230                 235                 240 ttc cgt tac gcc gcc ggc cag gga gtg gcc tcg atg gtc tgc ttc tac         768
Phe Arg Tyr Ala Ala Gly Gln Gly Val Ala Ser Met Val Cys Phe Tyr
                245                 250                 255 gga gtc ccg ctt ctg att gtc aat ggt ttc ctc gtg ttg atc act tac         816
Gly Val Pro Leu Leu Ile Val Asn Gly Phe Leu Val Leu Ile Thr Tyr
            260                 265                 270 ttg cag cac acg cat cct tcc ctg cct cac tac gat tcg tcc gag tgg         864
Leu Gln His Thr His Pro Ser Leu Pro His Tyr Asp Ser Ser Glu Trp
        275                 280                 285 gat tgg ttc agg gga gct ttg gct acc gtt gac aga gac tac gga atc         912
Asp Trp Phe Arg Gly Ala Leu Ala Thr Val Asp Arg Asp Tyr Gly Ile
    290                 295                 300 ttg aac aag gtc ttc cac aat att acc gac acg cac gtg gcc cat cat         960
Leu Asn Lys Val Phe His Asn Ile Thr Asp Thr His Val Ala His His
305                 310                 315                 320 ccg ttc tcc acg atg ccg cat tat cac gcg atg gaa gct acc aag gcg        1008
Pro Phe Ser Thr Met Pro His Tyr His Ala Met Glu Ala Thr Lys Ala
                325                 330                 335 ata aag ccg ata ctg gga gag tat tat cag ttc gat ggg acg ccg gtg        1056
Ile Lys Pro Ile Leu Gly Glu Tyr Tyr Gln Phe Asp Gly Thr Pro Val
            340                 345                 350 gtt aag gcg atg tgg agg gag gcg aag gag tgt atc tat gtg gaa ccg        1104
Val Lys Ala Met Trp Arg Glu Ala Lys Glu Cys Ile Tyr Val Glu Pro
        355                 360                 365 gac agg caa ggt gag aag aaa ggt gtg ttc tgg tac aac aat aag tta        1152
Asp Arg Gln Gly Glu Lys Lys Gly Val Phe Trp Tyr Asn Asn Lys Leu
    370                 375                 380 tga                                                                    1155

<210> SEQ ID NO 2
<211> LENGTH: 384
<212> TYPE: PRT
<213> ORGANISM: Brassica napus
<220> FEATURE:
<221> NAME/KEY: VARIANT
<222> LOCATION: 69
<223> OTHER INFORMATION: Xaa = Any Amino Acid

<400> SEQUENCE: 2

Met Gly Ala Gly Gly Arg Met Gln Val Ser Pro Pro Ser Lys Lys Ser
1               5                   10                  15
```

```
Glu Thr Asp Thr Ile Lys Arg Val Pro Cys Glu Thr Pro Pro Phe Thr
             20                  25                  30

Val Gly Glu Leu Lys Lys Ala Ile Pro Pro His Cys Phe Lys Arg Ser
         35                  40                  45

Ile Pro Arg Ser Phe Ser Tyr Leu Ile Trp Asp Ile Ile Ala Ser
     50                  55                  60

Cys Phe Tyr Tyr Xaa Ala Thr Thr Tyr Phe Pro Leu Leu Pro His Pro
 65              70                  75                      80

Leu Ser Tyr Phe Ala Trp Pro Leu Tyr Trp Ala Cys Gln Gly Cys Val
                 85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
            115                 120                 125

Phe Leu Leu Val Pro Tyr Phe Ser Trp Lys Tyr Ser His Arg Ser His
130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Arg
        195                 200                 205

Cys His Phe His Pro Asn Ala Pro Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240

Phe Arg Tyr Ala Ala Gly Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
        275                 280                 285

Asp Trp Phe Arg Gly Ala Leu Ala Thr Val Asp Arg Asp Tyr Gly Ile
    290                 295                 300

Leu Asn Lys Val Phe His Asn Ile Thr Asp Thr His Val Ala His His
305                 310                 315                 320

Pro Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
        355                 360                 365

Asp Arg Gln Gly Glu Lys Lys Gly Val Phe Trp Tyr Asn Asn Lys Leu
    370                 375                 380

<210> SEQ ID NO 3
<211> LENGTH: 1155
<212> TYPE: DNA
<213> ORGANISM: Brassica napus
<220> FEATURE:
<221> NAME/KEY: CDS
<222> LOCATION: (1)...(1152)
<223> OTHER INFORMATION: Clone: IMC129, G to A transversion mutation at
```

```
                nucleotide 316 of the D form
<220> FEATURE:
<221> NAME/KEY: misc_feature
<222> LOCATION: 205
<223> OTHER INFORMATION: n = A,T,C or G

<400> SEQUENCE: 3 atg ggt gca ggt gga aga atg caa gtg tct cct ccc tcc aag aag tct      48
Met Gly Ala Gly Gly Arg Met Gln Val Ser Pro Pro Ser Lys Lys Ser
1               5                   10                  15 gaa acc gac acc atc aag cgc gta ccc tgc gag aca ccg ccc ttc act      96
Glu Thr Asp Thr Ile Lys Arg Val Pro Cys Glu Thr Pro Pro Phe Thr
            20                  25                  30 gtc gga gaa ctc aag aaa gca atc cca ccg cac tgt ttc aaa cgc tcg     144
Val Gly Glu Leu Lys Lys Ala Ile Pro Pro His Cys Phe Lys Arg Ser
        35                  40                  45 atc cct cgc tct ttc tcc tac ctc atc tgg gac atc ata gcc tcc         192
Ile Pro Arg Ser Phe Ser Tyr Leu Ile Trp Asp Ile Ile Ala Ser
    50                  55                  60 tgc ttc tac tac ntc gcc acc act tac ttc cct ctc ctc cct cac cct     240
Cys Phe Tyr Tyr Xaa Ala Thr Thr Tyr Phe Pro Leu Leu Pro His Pro
65                  70                  75                  80 ctc tcc tac ttc gcc tgg cct ctc tac tgg gcc tgc caa ggg tgc gtc     288
Leu Ser Tyr Phe Ala Trp Pro Leu Tyr Trp Ala Cys Gln Gly Cys Val
                85                  90                  95 cta acc ggc gtc tgg gtc ata gcc cac aag tgc ggc cac cac gcc ttc     336
Leu Thr Gly Val Trp Val Ile Ala His Lys Cys Gly His His Ala Phe
            100                 105                 110 agc gac tac cag tgg ctt gac gac acc gtc ggt ctc atc ttc cac tcc     384
Ser Asp Tyr Gln Trp Leu Asp Asp Thr Val Gly Leu Ile Phe His Ser
        115                 120                 125 ttc ctc ctc gtc cct tac ttc tcc tgg aag tac agt cat cgc agc cac     432
Phe Leu Leu Val Pro Tyr Phe Ser Trp Lys Tyr Ser His Arg Ser His
    130                 135                 140 cat tcc aac act ggc tcc ctc gag aga gac gaa gtg ttt gtc ccc aag     480
His Ser Asn Thr Gly Ser Leu Glu Arg Asp Glu Val Phe Val Pro Lys
145                 150                 155                 160 aag aag tca gac atc aag tgg tac ggc aag tac ctc aac aac cct ttg     528
Lys Lys Ser Asp Ile Lys Trp Tyr Gly Lys Tyr Leu Asn Asn Pro Leu
                165                 170                 175 gga cgc acc gtg atg tta acg gtt cag ttc act ctc ggc tgg ccg ttg     576
Gly Arg Thr Val Met Leu Thr Val Gln Phe Thr Leu Gly Trp Pro Leu
            180                 185                 190 tac tta gcc ttc aac gtc tcg gga aga cct tac gac ggc ggc ttc cgt     624
Tyr Leu Ala Phe Asn Val Ser Gly Arg Pro Tyr Asp Gly Gly Phe Arg
        195                 200                 205 tgc cat ttc cac ccc aac gct ccc atc tac aac gac cgc gag cgt ctc     672
Cys His Phe His Pro Asn Ala Pro Ile Tyr Asn Asp Arg Glu Arg Leu
    210                 215                 220 cag ata tac atc tcc gac gct ggc atc ctc gcc gtc tgc tac ggt ctc     720
Gln Ile Tyr Ile Ser Asp Ala Gly Ile Leu Ala Val Cys Tyr Gly Leu
225                 230                 235                 240 ttc cgt tac gcc gcc ggc cag gga gtg gcc tcg atg gtc tgc ttc tac     768
Phe Arg Tyr Ala Ala Gly Gln Gly Val Ala Ser Met Val Cys Phe Tyr
                245                 250                 255 gga gtc ccg ctt ctg att gtc aat ggt ttc ctc gtg ttg atc act tac     816
Gly Val Pro Leu Leu Ile Val Asn Gly Phe Leu Val Leu Ile Thr Tyr
            260                 265                 270 ttg cag cac acg cat cct tcc ctg cct cac tac gat tcg tcc gag tgg     864
Leu Gln His Thr His Pro Ser Leu Pro His Tyr Asp Ser Ser Glu Trp
        275                 280                 285
```

```
gat tgg ttc agg gga gct ttg gct acc gtt gac aga gac tac gga atc    912
Asp Trp Phe Arg Gly Ala Leu Ala Thr Val Asp Arg Asp Tyr Gly Ile
290                 295                 300 ttg aac aag gtc ttc cac aat att acc gac acg cac gtg gcc cat cat    960
Leu Asn Lys Val Phe His Asn Ile Thr Asp Thr His Val Ala His His
305                 310                 315                 320 ccg ttc tcc acg atg ccg cat tat cac gcg atg gaa gct acc aag gcg   1008
Pro Phe Ser Thr Met Pro His Tyr His Ala Met Glu Ala Thr Lys Ala
                325                 330                 335 ata aag ccg ata ctg gga gag tat tat cag ttc gat ggg acg ccg gtg   1056
Ile Lys Pro Ile Leu Gly Glu Tyr Tyr Gln Phe Asp Gly Thr Pro Val
            340                 345                 350 gtt aag gcg atg tgg agg gag gcg aag gag tgt atc tat gtg gaa ccg   1104
Val Lys Ala Met Trp Arg Glu Ala Lys Glu Cys Ile Tyr Val Glu Pro
        355                 360                 365 gac agg caa ggt gag aag aaa ggt gtg ttc tgg tac aac aat aag tta   1152
Asp Arg Gln Gly Glu Lys Lys Gly Val Phe Trp Tyr Asn Asn Lys Leu
370                 375                 380 tga                                                                1155
```

<210> SEQ ID NO 4
<211> LENGTH: 384
<212> TYPE: PRT
<213> ORGANISM: Brassica napus
<220> FEATURE:
<221> NAME/KEY: VARIANT
<222> LOCATION: 69
<223> OTHER INFORMATION: Xaa = Any Amino Acid

<400> SEQUENCE: 4

```
Met Gly Ala Gly Gly Arg Met Gln Val Ser Pro Ser Lys Lys Ser
1               5                   10                  15

Glu Thr Asp Thr Ile Lys Arg Val Pro Cys Glu Thr Pro Pro Phe Thr
                20                  25                  30

Val Gly Glu Leu Lys Lys Ala Ile Pro Pro His Cys Phe Lys Arg Ser
            35                  40                  45

Ile Pro Arg Ser Phe Ser Tyr Leu Ile Trp Asp Ile Ile Ala Ser
50                  55                  60

Cys Phe Tyr Tyr Xaa Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Lys Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Arg
        195                 200                 205

Cys His Phe His Pro Asn Ala Pro Ile Tyr Asn Asp Arg Glu Arg Leu
```

-continued

```
                210                 215                 220
Gln Ile Tyr Ile Ser Asp Ala Gly Ile Leu Ala Val Cys Tyr Gly Leu
225                 230                 235                 240

Phe Arg Tyr Ala Ala Gly Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
        275                 280                 285

Asp Trp Phe Arg Gly Ala Leu Ala Thr Val Asp Arg Asp Tyr Gly Ile
290                 295                 300

Leu Asn Lys Val Phe His Asn Ile Thr Asp Thr His Val Ala His His
305                 310                 315                 320

Pro Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
        355                 360                 365

Asp Arg Gln Gly Glu Lys Lys Gly Val Phe Trp Tyr Asn Asn Lys Leu
370                 375                 380

<210> SEQ ID NO 5
<211> LENGTH: 1155
<212> TYPE: DNA
<213> ORGANISM: Brassica napus
<220> FEATURE:
<221> NAME/KEY: CDS
<222> LOCATION: (1)...(1152)
<223> OTHER INFORMATION: wild type F form

<400> SEQUENCE: 5 atg ggt gca ggt gga aga atg caa gtg tct cct ccc tcc aaa aag tct      48
Met Gly Ala Gly Gly Arg Met Gln Val Ser Pro Pro Ser Lys Lys Ser
1               5                   10                  15 gaa acc gac aac atc aag cgc gta ccc tgc gag aca ccg ccc ttc act      96
Glu Thr Asp Asn Ile Lys Arg Val Pro Cys Glu Thr Pro Pro Phe Thr
                20                  25                  30 gtc gga gaa ctc aag aaa gca atc cca ccg cac tgt ttc aaa cgc tcg     144
Val Gly Glu Leu Lys Lys Ala Ile Pro Pro His Cys Phe Lys Arg Ser
            35                  40                  45 atc cct cgc tct ttc tcc tac ctc atc tgg gac atc atc ata gcc tcc     192
Ile Pro Arg Ser Phe Ser Tyr Leu Ile Trp Asp Ile Ile Ile Ala Ser
        50                  55                  60 tgc ttc tac tac gtc gcc acc act tac ttc cct ctc ctc cct cac cct     240
Cys Phe Tyr Tyr Val Ala Thr Thr Tyr Phe Pro Leu Leu Pro His Pro
65                  70                  75                  80 ctc tcc tac ttc gcc tgg cct ctc tac tgg gcc tgc cag ggc tgc gtc     288
Leu Ser Tyr Phe Ala Trp Pro Leu Tyr Trp Ala Cys Gln Gly Cys Val
                85                  90                  95 cta acc ggc gtc tgg gtc ata gcc cac gag tgc ggc cac cac gcc ttc     336
Leu Thr Gly Val Trp Val Ile Ala His Glu Cys Gly His His Ala Phe
            100                 105                 110 agc gac tac cag tgg ctg gac gac acc gtc ggc ctc atc ttc cac tcc     384
Ser Asp Tyr Gln Trp Leu Asp Asp Thr Val Gly Leu Ile Phe His Ser
        115                 120                 125 ttc ctc ctc gtc cct tac ttc tcc tgg aag tac agt cat cga cgc cac     432
Phe Leu Leu Val Pro Tyr Phe Ser Trp Lys Tyr Ser His Arg Arg His
    130                 135                 140
```

```
cat tcc aac act ggc tcc ctc gag aga gac gaa gtg ttt gtc ccc aag      480
His Ser Asn Thr Gly Ser Leu Glu Arg Asp Glu Val Phe Val Pro Lys
145                 150                 155                 160 aag aag tca gac atc aag tgg tac ggc aag tac ctc aac aac cct ttg      528
Lys Lys Ser Asp Ile Lys Trp Tyr Gly Lys Tyr Leu Asn Asn Pro Leu
                165                 170                 175 gga cgc acc gtg atg tta acg gtt cag ttc act ctc ggc tgg cct ttg      576
Gly Arg Thr Val Met Leu Thr Val Gln Phe Thr Leu Gly Trp Pro Leu
            180                 185                 190 tac tta gcc ttc aac gtc tcg ggg aga cct tac gac ggc ggc ttc gct      624
Tyr Leu Ala Phe Asn Val Ser Gly Arg Pro Tyr Asp Gly Gly Phe Ala
        195                 200                 205 tgc cat ttc cac ccc aac gct ccc atc tac aac gac cgc gag cgt ctc      672
Cys His Phe His Pro Asn Ala Pro Ile Tyr Asn Asp Arg Glu Arg Leu
    210                 215                 220 cag ata tac atc tcc gac gct ggc atc ctc gcc gtc tgc tac ggt ctc      720
Gln Ile Tyr Ile Ser Asp Ala Gly Ile Leu Ala Val Cys Tyr Gly Leu
225                 230                 235                 240 tac cgc tac gct gct gtc caa gga gtt gcc tcg atg gtc tgc ttc tac      768
Tyr Arg Tyr Ala Ala Val Gln Gly Val Ala Ser Met Val Cys Phe Tyr
                245                 250                 255 gga gtt ccg ctt ctg att gtc aat ggg ttc tta gtt ttg atc act tac      816
Gly Val Pro Leu Leu Ile Val Asn Gly Phe Leu Val Leu Ile Thr Tyr
            260                 265                 270 ttg cag cac acg cat cct tcc ctg cct cac tat gac tcg tct gag tgg      864
Leu Gln His Thr His Pro Ser Leu Pro His Tyr Asp Ser Ser Glu Trp
        275                 280                 285 gat tgg ttg agg gga gct ttg gcc acc gtt gac aga gac tac gga atc      912
Asp Trp Leu Arg Gly Ala Leu Ala Thr Val Asp Arg Asp Tyr Gly Ile
    290                 295                 300 ttg aac aag gtc ttc cac aat atc acg gac acg cac gtg gcg cat cac      960
Leu Asn Lys Val Phe His Asn Ile Thr Asp Thr His Val Ala His His
305                 310                 315                 320 ctg ttc tcg acc atg ccg cat tat cat gcg atg gaa gct acg aag gcg     1008
Leu Phe Ser Thr Met Pro His Tyr His Ala Met Glu Ala Thr Lys Ala
                325                 330                 335 ata aag ccg ata ctg gga gag tat tat cag ttg cat ggg acg ccg gtg     1056
Ile Lys Pro Ile Leu Gly Glu Tyr Tyr Gln Leu His Gly Thr Pro Val
            340                 345                 350 gtt aag gcg atg tgg agg gag gcg aag gag tgt atc tat gtg gaa ccg     1104
Val Lys Ala Met Trp Arg Glu Ala Lys Glu Cys Ile Tyr Val Glu Pro
        355                 360                 365 gac agg caa ggt gag aag aaa ggt gtg ttc tgg tac aac aat aag tta     1152
Asp Arg Gln Gly Glu Lys Lys Gly Val Phe Trp Tyr Asn Asn Lys Leu
    370                 375                 380 tga                                                                  1155

<210> SEQ ID NO 6
<211> LENGTH: 384
<212> TYPE: PRT
<213> ORGANISM: Brassica napus

<400> SEQUENCE: 6

Met Gly Ala Gly Gly Arg Met Gln Val Ser Pro Pro Ser Lys Lys Ser
1               5                   10                  15

Glu Thr Asp Asn Ile Lys Arg Val Pro Cys Glu Thr Pro Pro Phe Thr
                20                  25                  30

Val Gly Glu Leu Lys Lys Ala Ile Pro Pro His Cys Phe Lys Arg Ser
            35                  40                  45
```

-continued

```
Ile Pro Arg Ser Phe Ser Tyr Leu Ile Trp Asp Ile Ile Ala Ser
     50                  55                  60
Cys Phe Tyr Tyr Val Ala Thr Thr Tyr Phe Pro Leu Leu Pro His Pro
 65                  70                  75                  80
Leu Ser Tyr Phe Ala Trp Pro Leu Tyr Trp Ala Cys Gln Gly Cys Val
                 85                  90                  95
Leu Thr Gly Val Trp Val Ile Ala His Glu Cys Gly His His Ala Phe
            100                 105                 110
Ser Asp Tyr Gln Trp Leu Asp Asp Thr Val Gly Leu Ile Phe His Ser
            115                 120                 125
Phe Leu Leu Val Pro Tyr Phe Ser Trp Lys Tyr Ser His Arg Arg His
    130                 135                 140
His Ser Asn Thr Gly Ser Leu Glu Arg Asp Glu Val Phe Val Pro Lys
145                 150                 155                 160
Lys Lys Ser Asp Ile Lys Trp Tyr Gly Lys Tyr Leu Asn Asn Pro Leu
                165                 170                 175
Gly Arg Thr Val Met Leu Thr Val Gln Phe Thr Leu Gly Trp Pro Leu
            180                 185                 190
Tyr Leu Ala Phe Asn Val Ser Gly Arg Pro Tyr Asp Gly Gly Phe Ala
        195                 200                 205
Cys His Phe His Pro Asn Ala Pro Ile Tyr Asn Asp Arg Glu Arg Leu
210                 215                 220
Gln Ile Tyr Ile Ser Asp Ala Gly Ile Leu Ala Val Cys Tyr Gly Leu
225                 230                 235                 240
Tyr Arg Tyr Ala Ala Val Gln Gly Val Ala Ser Met Val Cys Phe Tyr
                245                 250                 255
Gly Val Pro Leu Leu Ile Val Asn Gly Phe Leu Val Leu Ile Thr Tyr
            260                 265                 270
Leu Gln His Thr His Pro Ser Leu Pro His Tyr Asp Ser Ser Glu Trp
    275                 280                 285
Asp Trp Leu Arg Gly Ala Leu Ala Thr Val Asp Arg Asp Tyr Gly Ile
290                 295                 300
Leu Asn Lys Val Phe His Asn Ile Thr Asp Thr His Val Ala His His
305                 310                 315                 320
Leu Phe Ser Thr Met Pro His Tyr His Ala Met Glu Ala Thr Lys Ala
                325                 330                 335
Ile Lys Pro Ile Leu Gly Glu Tyr Tyr Gln Leu His Gly Thr Pro Val
            340                 345                 350
Val Lys Ala Met Trp Arg Glu Ala Lys Glu Cys Ile Tyr Val Glu Pro
        355                 360                 365
Asp Arg Gln Gly Glu Lys Lys Gly Val Phe Trp Tyr Asn Asn Lys Leu
    370                 375                 380
```

<210> SEQ ID NO 7
<211> LENGTH: 1155
<212> TYPE: DNA
<213> ORGANISM: Brassica napus
<220> FEATURE:
<221> NAME/KEY: CDS
<222> LOCATION: (1)...(1152)
<223> OTHER INFORMATION: Clone: Q508, T to A transversion mutation at
      nucleotide 515 of the F form

<400> SEQUENCE: 7

```
atg ggt gca ggt gga aga atg caa gtg tct cct ccc tcc aaa aag tct    48
Met Gly Ala Gly Gly Arg Met Gln Val Ser Pro Pro Ser Lys Lys Ser
```

-continued

```
                1               5                      10                     15
gaa   acc   gac   aac   atc   aag   cgc   gta   ccc   tgc   gag   aca   ccg   ccc   ttc   act        96
Glu   Thr   Asp   Asn   Ile   Lys   Arg   Val   Pro   Cys   Glu   Thr   Pro   Pro   Phe   Thr
                        20                      25                      30 gtc   gga   gaa   ctc   aag   aaa   gca   atc   cca   ccg   cac   tgt   ttc   aaa   cgc   tcg       144
Val   Gly   Glu   Leu   Lys   Lys   Ala   Ile   Pro   Pro   His   Cys   Phe   Lys   Arg   Ser
            35                      40                      45 atc   cct   cgc   tct   ttc   tcc   tac   ctc   atc   tgg   gac   atc   atc   ata   gcc   tcc       192
Ile   Pro   Arg   Ser   Phe   Ser   Tyr   Leu   Ile   Trp   Asp   Ile   Ile   Ile   Ala   Ser
      50                      55                      60 tgc   ttc   tac   tac   gtc   gcc   acc   act   tac   ttc   cct   ctc   ctc   cct   cac   cct       240
Cys   Phe   Tyr   Tyr   Val   Ala   Thr   Thr   Tyr   Phe   Pro   Leu   Leu   Pro   His   Pro
65                      70                      75                      80 ctc   tcc   tac   ttc   gcc   tgg   cct   ctc   tac   tgg   gcc   tgc   cag   ggc   tgc   gtc       288
Leu   Ser   Tyr   Phe   Ala   Trp   Pro   Leu   Tyr   Trp   Ala   Cys   Gln   Gly   Cys   Val
                  85                      90                      95 cta   acc   ggc   gtc   tgg   gtc   ata   gcc   cac   gag   tgc   ggc   cac   cac   gcc   ttc       336
Leu   Thr   Gly   Val   Trp   Val   Ile   Ala   His   Glu   Cys   Gly   His   His   Ala   Phe
            100                     105                     110 agc   gac   tac   cag   tgg   ctg   gac   gac   acc   gtc   ggc   ctc   atc   ttc   cac   tcc       384
Ser   Asp   Tyr   Gln   Trp   Leu   Asp   Asp   Thr   Val   Gly   Leu   Ile   Phe   His   Ser
      115                     120                     125 ttc   ctc   ctc   gtc   cct   tac   ttc   tcc   tgg   aag   tac   agt   cat   cga   cgc   cac       432
Phe   Leu   Leu   Val   Pro   Tyr   Phe   Ser   Trp   Lys   Tyr   Ser   His   Arg   Arg   His
130                     135                     140 cat   tcc   aac   act   ggc   tcc   ctc   gag   aga   gac   gaa   gtg   ttt   gtc   ccc   aag       480
His   Ser   Asn   Thr   Gly   Ser   Leu   Glu   Arg   Asp   Glu   Val   Phe   Val   Pro   Lys
145                     150                     155                     160 aag   aag   tca   gac   atc   aag   tgg   tac   ggc   aag   tac   cac   aac   aac   cct   ttg       528
Lys   Lys   Ser   Asp   Ile   Lys   Trp   Tyr   Gly   Lys   Tyr   His   Asn   Asn   Pro   Leu
                  165                     170                     175 gga   cgc   acc   gtg   atg   tta   acg   gtt   cag   ttc   act   ctc   ggc   tgg   cct   ttg       576
Gly   Arg   Thr   Val   Met   Leu   Thr   Val   Gln   Phe   Thr   Leu   Gly   Trp   Pro   Leu
            180                     185                     190 tac   tta   gcc   ttc   aac   gtc   tcg   ggg   aga   cct   tac   gac   ggc   ggc   ttc   gct       624
Tyr   Leu   Ala   Phe   Asn   Val   Ser   Gly   Arg   Pro   Tyr   Asp   Gly   Gly   Phe   Ala
      195                     200                     205 tgc   cat   ttc   cac   ccc   aac   gct   ccc   atc   tac   aac   gac   cgc   gag   cgt   ctc       672
Cys   His   Phe   His   Pro   Asn   Ala   Pro   Ile   Tyr   Asn   Asp   Arg   Glu   Arg   Leu
210                     215                     220 cag   ata   tac   atc   tcc   gac   gct   ggc   atc   ctc   gcc   gtc   tgc   tac   ggt   ctc       720
Gln   Ile   Tyr   Ile   Ser   Asp   Ala   Gly   Ile   Leu   Ala   Val   Cys   Tyr   Gly   Leu
225                     230                     235                     240 tac   cgc   tac   gct   gct   gtc   caa   gga   gtt   gcc   tcg   atg   gtc   tgc   ttc   tac       768
Tyr   Arg   Tyr   Ala   Ala   Val   Gln   Gly   Val   Ala   Ser   Met   Val   Cys   Phe   Tyr
                  245                     250                     255 gga   gtt   ccg   ctt   ctg   att   gtc   aat   ggg   ttc   tta   gtt   ttg   atc   act   tac       816
Gly   Val   Pro   Leu   Leu   Ile   Val   Asn   Gly   Phe   Leu   Val   Leu   Ile   Thr   Tyr
            260                     265                     270 ttg   cag   cac   acg   cat   cct   tcc   ctg   cct   cac   tat   gac   tcg   tct   gag   tgg       864
Leu   Gln   His   Thr   His   Pro   Ser   Leu   Pro   His   Tyr   Asp   Ser   Ser   Glu   Trp
      275                     280                     285 gat   tgg   ttg   agg   gga   gct   ttg   gcc   acc   gtt   gac   aga   gac   tac   gga   atc       912
Asp   Trp   Leu   Arg   Gly   Ala   Leu   Ala   Thr   Val   Asp   Arg   Asp   Tyr   Gly   Ile
290                     295                     300 ttg   aac   aag   gtc   ttc   cac   aat   atc   acg   gac   acg   cac   gtg   gcg   cat   cac       960
Leu   Asn   Lys   Val   Phe   His   Asn   Ile   Thr   Asp   Thr   His   Val   Ala   His   His
305                     310                     315                     320 ctg   ttc   tcg   acc   atg   ccg   cat   tat   cat   gcg   atg   gaa   gct   acg   aag   gcg      1008
```

```
Leu Phe Ser Thr Met Pro His Tyr His Ala Met Glu Ala Thr Lys Ala
                325                 330                 335 ata aag ccg ata ctg gga gag tat tat cag ttg cat ggg acg ccg gtg    1056
Ile Lys Pro Ile Leu Gly Glu Tyr Tyr Gln Leu His Gly Thr Pro Val
            340                 345                 350 gtt aag gcg atg tgg agg gag gcg aag gag tgt atc tat gtg gaa ccg    1104
Val Lys Ala Met Trp Arg Glu Ala Lys Glu Cys Ile Tyr Val Glu Pro
        355                 360                 365 gac agg caa ggt gag aag aaa ggt gtg ttc tgg tac aat aat aag tta    1152
Asp Arg Gln Gly Glu Lys Lys Gly Val Phe Trp Tyr Asn Asn Lys Leu
    370                 375                 380 tga                                                                1155
```

<210> SEQ ID NO 8
<211> LENGTH: 384
<212> TYPE: PRT
<213> ORGANISM: Brassica napus

<400> SEQUENCE: 8

```
Met Gly Ala Gly Gly Arg Met Gln Val Ser Pro Pro Ser Lys Lys Ser
 1               5                  10                  15

Glu Thr Asp Asn Ile Lys Arg Val Pro Cys Glu Thr Pro Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr His Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
        195                 200                 205

Cys His Phe His Pro Asn Ala Pro Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
        275                 280                 285
```

-continued

```
Asp Trp Leu Arg Gly Ala Leu Ala Thr Val Asp Arg Asp Tyr Gly Ile
    290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Leu His Gly Thr Pro Val
            340                 345                 350

Val Lys Ala Met Trp Arg Glu Ala Lys Glu Cys Ile Tyr Val Glu Pro
        355                 360                 365

Asp Arg Gln Gly Glu Lys Lys Gly Val Phe Trp Tyr Asn Asn Lys Leu
    370                 375                 380
```

<210> SEQ ID NO 9
<211> LENGTH: 5
<212> TYPE: PRT
<213> ORGANISM: Brassica napus

<400> SEQUENCE: 9

```
His Glu Cys Gly His
1               5
```

<210> SEQ ID NO 10
<211> LENGTH: 5
<212> TYPE: PRT
<213> ORGANISM: Brassica napus

<400> SEQUENCE: 10

```
His Lys Cys Gly His
1               5
```

<210> SEQ ID NO 11
<211> LENGTH: 5
<212> TYPE: PRT
<213> ORGANISM: Arabidopsis thaliana

<400> SEQUENCE: 11

```
His Arg Arg His His
1               5
```

<210> SEQ ID NO 12
<211> LENGTH: 5
<212> TYPE: PRT
<213> ORGANISM: Arabidopsis thaliana

<400> SEQUENCE: 12

```
His Val Ala His His
1               5
```

<210> SEQ ID NO 13
<211> LENGTH: 6
<212> TYPE: PRT
<213> ORGANISM: Brassica napus

<400> SEQUENCE: 13

```
Lys Tyr Leu Asn Asn Pro
1               5
```

<210> SEQ ID NO 14
<211> LENGTH: 5
<212> TYPE: PRT
<213> ORGANISM: Brassica napus

```
<400> SEQUENCE: 14

Lys Tyr His Asn Asn
 1               5

<210> SEQ ID NO 15
<211> LENGTH: 30
<212> TYPE: PRT
<213> ORGANISM: Arabidopsis thaliana

<400> SEQUENCE: 15

Ile Trp Val Ile Ala His Glu Cys Gly His His Ala Phe Ser Asp Tyr
 1               5                  10                  15

Gln Trp Leu Asp Asp Thr Val Gly Leu Ile Phe His Ser Phe
            20                  25                  30

<210> SEQ ID NO 16
<211> LENGTH: 30
<212> TYPE: PRT
<213> ORGANISM: Glycine max

<400> SEQUENCE: 16

Val Trp Val Ile Ala His Glu Cys Gly His His Ala Phe Ser Lys Tyr
 1               5                  10                  15

Gln Trp Val Asp Asp Val Val Gly Leu Thr Leu His Ser Thr
            20                  25                  30

<210> SEQ ID NO 17
<211> LENGTH: 30
<212> TYPE: PRT
<213> ORGANISM: Zea mays

<400> SEQUENCE: 17

Val Trp Val Ile Ala His Glu Cys Gly His His Ala Phe Ser Asp Tyr
 1               5                  10                  15

Ser Leu Leu Asp Asp Val Val Gly Leu Val Leu His Ser Ser
            20                  25                  30

<210> SEQ ID NO 18
<211> LENGTH: 29
<212> TYPE: PRT
<213> ORGANISM: Ricinus communis

<400> SEQUENCE: 18

Trp Val Met Ala His Asp Cys Gly His His Ala Phe Ser Asp Tyr Gln
 1               5                  10                  15

Leu Leu Asp Asp Val Val Gly Leu Ile Leu His Ser Cys
            20                  25

<210> SEQ ID NO 19
<211> LENGTH: 29
<212> TYPE: PRT
<213> ORGANISM: Brassica napus

<400> SEQUENCE: 19

Val Trp Val Ile Ala His Glu Cys Gly His His Ala Phe Ser Asp Tyr
 1               5                  10                  15

Gln Trp Leu Asp Asp Thr Val Gly Leu Ile Phe His Ser
            20                  25

<210> SEQ ID NO 20
<211> LENGTH: 29
<212> TYPE: PRT
```

<213> ORGANISM: Arabidopsis thaliana

<400> SEQUENCE: 20

```
Leu Leu Val Pro Tyr Phe Ser Trp Lys Tyr Ser His Arg Arg His His
1               5                   10                  15

Ser Asn Thr Gly Ser Leu Glu Arg Asp Glu Val Phe Val
            20                  25
```

<210> SEQ ID NO 21
<211> LENGTH: 29
<212> TYPE: PRT
<213> ORGANISM: Glycine max

<400> SEQUENCE: 21

```
Leu Leu Val Pro Tyr Phe Ser Trp Lys Ile Ser His Arg Arg His His
1               5                   10                  15

Ser Asn Thr Gly Ser Leu Asp Arg Asp Glu Val Phe Val
            20                  25
```

<210> SEQ ID NO 22
<211> LENGTH: 29
<212> TYPE: PRT
<213> ORGANISM: Zea mays

<400> SEQUENCE: 22

```
Leu Met Val Pro Tyr Phe Ser Trp Lys Tyr Ser His Arg Arg His His
1               5                   10                  15

Ser Asn Thr Gly Ser Leu Glu Arg Asp Glu Val Phe Val
            20                  25
```

<210> SEQ ID NO 23
<211> LENGTH: 29
<212> TYPE: PRT
<213> ORGANISM: Ricinus communis

<400> SEQUENCE: 23

```
Leu Leu Val Pro Tyr Phe Ser Trp Lys His Ser His Arg Arg His His
1               5                   10                  15

Ser Asn Thr Gly Ser Leu Glu Arg Asp Glu Val Phe Val
            20                  25
```

<210> SEQ ID NO 24
<211> LENGTH: 29
<212> TYPE: PRT
<213> ORGANISM: Brassica napus

<400> SEQUENCE: 24

```
Leu Leu Val Pro Tyr Phe Ser Trp Lys Tyr Ser His Arg Ser His His
1               5                   10                  15

Ser Asn Thr Gly Ser Leu Glu Arg Asp Glu Val Phe Val
            20                  25
```

<210> SEQ ID NO 25
<211> LENGTH: 36
<212> TYPE: PRT
<213> ORGANISM: Arabidopsis thaliana

<400> SEQUENCE: 25

```
Asp Arg Asp Tyr Gly Ile Leu Asn Lys Val Phe His Asn Ile Thr Asp
1               5                   10                  15

Thr His Val Ala His His Leu Phe Ser Thr Met Pro His Tyr Asn Ala
            20                  25                  30
```

Met Glu Ala Thr
        35

<210> SEQ ID NO 26
<211> LENGTH: 36
<212> TYPE: PRT
<213> ORGANISM: Glycine max

<400> SEQUENCE: 26

Asp Arg Asp Tyr Gly Ile Leu Asn Lys Val Phe His His Ile Thr Asp
1               5                   10                  15

Thr His Val Ala His His Leu Phe Ser Thr Met Pro His Tyr His Ala
            20                  25                  30

Met Glu Ala Thr
        35

<210> SEQ ID NO 27
<211> LENGTH: 36
<212> TYPE: PRT
<213> ORGANISM: Zea mays

<400> SEQUENCE: 27

Asp Arg Asp Tyr Gly Ile Leu Asn Arg Val Phe His Asn Ile Thr Asp
1               5                   10                  15

Thr His Val Ala His His Leu Phe Ser Thr Met Pro His Tyr His Ala
            20                  25                  30

Met Glu Ala Thr
        35

<210> SEQ ID NO 28
<211> LENGTH: 27
<212> TYPE: PRT
<213> ORGANISM: Ricinus communis

<400> SEQUENCE: 28

Asp Arg Asp Tyr Gly Ile Leu Asn Lys Val Phe His Asn Ile Thr Asp
1               5                   10                  15

Thr Gln Val Ala His His Leu Phe Thr Met Pro
            20                  25

<210> SEQ ID NO 29
<211> LENGTH: 36
<212> TYPE: PRT
<213> ORGANISM: Brassica napus

<400> SEQUENCE: 29

Asp Arg Asp Tyr Gly Ile Leu Asn Lys Val Phe His Asn Ile Thr Asp
1               5                   10                  15

Thr His Val Ala His His Pro Phe Ser Thr Met Pro His Tyr His Ala
            20                  25                  30

Met Glu Ala Thr
        35

<210> SEQ ID NO 30
<211> LENGTH: 16
<212> TYPE: PRT
<213> ORGANISM: Arabidopsis thaliana

<400> SEQUENCE: 30

Ile Lys Trp Tyr Gly Lys Tyr Leu Asn Asn Pro Leu Gly Arg Ile Met
1               5                   10                  15

-continued

```
<210> SEQ ID NO 31
<211> LENGTH: 16
<212> TYPE: PRT
<213> ORGANISM: Glycine max

<400> SEQUENCE: 31

Val Ala Trp Phe Ser Leu Tyr Leu Asn Asn Pro Leu Gly Arg Ala Val
 1               5                  10                  15

<210> SEQ ID NO 32
<211> LENGTH: 16
<212> TYPE: PRT
<213> ORGANISM: Zea mays

<400> SEQUENCE: 32

Pro Trp Tyr Thr Pro Tyr Val Tyr Asn Asn Pro Val Gly Arg Val Val
 1               5                  10                  15

<210> SEQ ID NO 33
<211> LENGTH: 16
<212> TYPE: PRT
<213> ORGANISM: Ricinus communis

<400> SEQUENCE: 33

Ile Arg Trp Tyr Ser Lys Tyr Leu Asn Asn Pro Pro Gly Arg Ile Met
 1               5                  10                  15

<210> SEQ ID NO 34
<211> LENGTH: 16
<212> TYPE: PRT
<213> ORGANISM: Brassica napus

<400> SEQUENCE: 34

Ile Lys Trp Tyr Gly Lys Tyr Leu Asn Asn Pro Leu Gly Arg Thr Val
 1               5                  10                  15

<210> SEQ ID NO 35
<211> LENGTH: 22
<212> TYPE: PRT
<213> ORGANISM: Arabidopsis thaliana

<400> SEQUENCE: 35

Trp Ala Leu Phe Val Leu Gly His Asp Cys Gly His Gly Ser Phe Ser
 1               5                  10                  15

Asn Asp Pro Lys Leu Asn
            20

<210> SEQ ID NO 36
<211> LENGTH: 22
<212> TYPE: PRT
<213> ORGANISM: Brassica napus

<400> SEQUENCE: 36

Trp Ala Leu Phe Val Leu Gly His Asp Cys Gly His Gly Ser Phe Ser
 1               5                  10                  15

Asn Asp Pro Arg Leu Asn
            20

<210> SEQ ID NO 37
<211> LENGTH: 22
<212> TYPE: PRT
<213> ORGANISM: Glycine max
```

```
<400> SEQUENCE: 37

Trp Ala Leu Phe Val Leu Gly His Asp Cys Gly His Gly Ser Phe Ser
 1               5                  10                  15

Asn Asn Ser Lys Leu Asn
            20

<210> SEQ ID NO 38
<211> LENGTH: 22
<212> TYPE: PRT
<213> ORGANISM: Arabidopsis thaliana

<400> SEQUENCE: 38

Trp Ala Ile Phe Val Leu Gly His Asp Cys Gly His Gly Ser Phe Ser
 1               5                  10                  15

Asp Ile Pro Leu Leu Asn
            20

<210> SEQ ID NO 39
<211> LENGTH: 22
<212> TYPE: PRT
<213> ORGANISM: Glycine max

<400> SEQUENCE: 39

Trp Ala Leu Phe Val Leu Gly His Asp Cys Gly His Gly Ser Phe Ser
 1               5                  10                  15

Asp Ser Pro Pro Leu Asn
            20

<210> SEQ ID NO 40
<211> LENGTH: 6
<212> TYPE: PRT
<213> ORGANISM: Brassica napus

<400> SEQUENCE: 40

Ala His Lys Cys Gly His
 1               5

<210> SEQ ID NO 41
<211> LENGTH: 6
<212> TYPE: PRT
<213> ORGANISM: Brassica napus

<400> SEQUENCE: 41

Ala His Glu Cys Gly His
 1               5

<210> SEQ ID NO 42
<211> LENGTH: 6
<212> TYPE: PRT
<213> ORGANISM: Brassica napus

<400> SEQUENCE: 42

Gly His Asp Cys Ala His
 1               5

<210> SEQ ID NO 43
<211> LENGTH: 6
<212> TYPE: PRT
<213> ORGANISM: Brassica napus

<400> SEQUENCE: 43

Gly His Asp Cys Gly His
 1               5
```

-continued

```
<210> SEQ ID NO 44
<211> LENGTH: 21
<212> TYPE: DNA
<213> ORGANISM: Artificial Sequence
<220> FEATURE:
<223> OTHER INFORMATION: primer

<400> SEQUENCE: 44
ggatatgatg atggtgaaag a                                              21

<210> SEQ ID NO 45
<211> LENGTH: 21
<212> TYPE: DNA
<213> ORGANISM: Artificial Sequence
<220> FEATURE:
<223> OTHER INFORMATION: primer

<400> SEQUENCE: 45
tctttcacca tcatcatatc c                                              21

<210> SEQ ID NO 46
<211> LENGTH: 21
<212> TYPE: DNA
<213> ORGANISM: Artificial Sequence
<220> FEATURE:
<223> OTHER INFORMATION: primer

<400> SEQUENCE: 46
gttatgaagc aaagaagaaa c                                              21

<210> SEQ ID NO 47
<211> LENGTH: 21
<212> TYPE: DNA
<213> ORGANISM: Artificial Sequence
<220> FEATURE:
<223> OTHER INFORMATION: primer

<400> SEQUENCE: 47
gtttcttctt tgcttcataa c                                              21

<210> SEQ ID NO 48
<211> LENGTH: 29
<212> TYPE: PRT
<213> ORGANISM: Brassica napus

<400> SEQUENCE: 48

Leu Leu Val Pro Tyr Phe Ser Trp Lys Tyr Ser His Arg Arg His
 1               5                  10                  15

Ser Asn Thr Gly Ser Leu Glu Arg Asp Glu Val Phe Val
             20                  25

<210> SEQ ID NO 49
<211> LENGTH: 36
<212> TYPE: PRT
<213> ORGANISM: Brassica napus

<400> SEQUENCE: 49

Asp Arg Asp Tyr Gly Ile Leu Asn Lys Val Phe His Asn Ile Thr Asp
 1               5                  10                  15

Thr His Val Ala His His Leu Phe Ser Thr Met Pro His Tyr His Ala
             20                  25                  30

Met Glu Ala Thr
         35
```